US011849379B1

(12) United States Patent
Vanetik et al.

(10) Patent No.: US 11,849,379 B1
(45) Date of Patent: Dec. 19, 2023

(54) UNIVERSAL MOBILE ALERT SYSTEM AND METHOD

(71) Applicants: Anatoly Vanetik, Santa Ana, CA (US); Boris Braslavsky, Marina Del Rey, CA (US); Yuri Vanetik, Santa Ana, CA (US); Alexander Braslavsky, Laguna Beach, CA (US)

(72) Inventors: Anatoly Vanetik, Santa Ana, CA (US); Boris Braslavsky, Marina Del Rey, CA (US); Yuri Vanetik, Santa Ana, CA (US); Alexander Braslavsky, Laguna Beach, CA (US)

(73) Assignee: PUMASLIFE I LLC, Cheyenne, WY (US)

(*) Notice: Subject to any disclaimer, the term of this patent is extended or adjusted under 35 U.S.C. 154(b) by 0 days.

(21) Appl. No.: 18/212,676

(22) Filed: Jun. 21, 2023

Related U.S. Application Data

(60) Provisional application No. 63/470,116, filed on May 31, 2023.

(51) Int. Cl.
| | |
|---|---|
| *H04W 4/90* | (2018.01) |
| *G16H 50/20* | (2018.01) |
| *G16H 40/67* | (2018.01) |
| *H04W 4/021* | (2018.01) |

(52) U.S. Cl.
CPC ............. *H04W 4/90* (2018.02); *G16H 40/67* (2018.01); *G16H 50/20* (2018.01); *H04W 4/021* (2013.01)

(58) Field of Classification Search
CPC ..... H04W 4/021; H04W 4/022; H04W 4/023; H04W 4/029; H04W 4/90; G16H 40/67; G16H 50/20
See application file for complete search history.

(56) References Cited

U.S. PATENT DOCUMENTS

| | | | | |
|---|---|---|---|---|
| 9,374,698 | B2* | 6/2016 | Ahmed | ................... H04W 4/90 |
| 10,204,704 | B1* | 2/2019 | Wurst | .................... G16H 10/20 |
| 2010/0177644 | A1* | 7/2010 | Kucharczyk | ........ H04L 41/0681 |
| | | | | 370/250 |
| 2010/0219241 | A1* | 9/2010 | Corwin | .................. G16H 10/60 |
| | | | | 235/494 |
| 2014/0104059 | A1* | 4/2014 | Tran | ........................ G16Z 99/00 |
| | | | | 340/539.12 |
| 2014/0163425 | A1* | 6/2014 | Tran | ........................ A61B 7/00 |
| | | | | 600/595 |
| 2014/0243635 | A1* | 8/2014 | Arefieg | ............ A61B 5/150854 |
| | | | | 600/365 |
| 2014/0253324 | A1* | 9/2014 | Tamez | ............... G08B 21/0461 |
| | | | | 340/539.12 |

(Continued)

*Primary Examiner* — Jean A Gelin
(74) *Attorney, Agent, or Firm* — Snell & Wilmer LLP

(57) ABSTRACT

A system for monitoring a user and coordinating one or more alert response by one or more first responders and configured to connect to one or more monitoring devices. The system includes a mobile device configured to perform operations. The operations include obtain user data from a continuous user data stream from the one or more monitoring devices, determine, based on the user data stream and user historical records, a safe zone of the user, and determine, based on a user data stream and user historical records, whether a current state or a predicted state of the user is within the safe zone and/or a danger zone defined as being outside the safe zone.

20 Claims, 6 Drawing Sheets

(56) References Cited

U.S. PATENT DOCUMENTS

| | | | | |
|---|---|---|---|---|
| 2015/0288797 | A1* | 10/2015 | Vincent | G16H 10/60 |
| | | | | 455/404.2 |
| 2016/0131755 | A1* | 5/2016 | Wijbrans | G01S 13/74 |
| | | | | 342/458 |
| 2016/0310005 | A1* | 10/2016 | Pekander | A61B 5/6803 |
| 2017/0039832 | A1* | 2/2017 | Chen | G08B 21/028 |
| 2017/0169699 | A1* | 6/2017 | Will | H04W 4/90 |
| 2018/0174430 | A1* | 6/2018 | Sieja | G08B 21/0453 |
| 2018/0352085 | A1* | 12/2018 | Philbin | H04L 67/146 |
| 2019/0162598 | A1* | 5/2019 | Koenen | G01J 3/50 |
| 2019/0197861 | A1* | 6/2019 | Tunnell | G08B 21/0492 |
| 2019/0206549 | A1* | 7/2019 | Perry | G06Q 10/06311 |
| 2020/0390195 | A1* | 12/2020 | Sun | A43B 5/048 |
| 2021/0193336 | A1* | 6/2021 | Nemeth | G08B 25/10 |
| 2021/0281992 | A1* | 9/2021 | Selanders | H04W 76/14 |
| 2022/0058399 | A1* | 2/2022 | Neser | G06V 20/54 |
| 2022/0172625 | A1* | 6/2022 | Chou | G08G 1/0116 |
| 2023/0106214 | A1* | 4/2023 | Hsu | H04L 65/764 |
| | | | | 709/219 |

\* cited by examiner

400

```
┌─────────────────────────────────────────────────────────┐
│       OBTAIN USER DATA STREAM ASSOCIATED WITH A USER    │
│                           455                           │
└─────────────────────────────────────────────────────────┘
                             │
                             ▼
┌─────────────────────────────────────────────────────────┐
│   TRANSMIT THE USER DATA STREAM TO AT LEAST ONE OF A    │
│   CLOUD, A SERVER, AND/OR ANOTHER CONNECTED DEVICE      │
│                           465                           │
└─────────────────────────────────────────────────────────┘
                             │
                             ▼
┌─────────────────────────────────────────────────────────┐
│   DETERMINE A SAFE ZONE OF THE USER BASED ON USER       │
│   HISTORICAL RECORDS AND THE USER DATA STREAM           │
│                           465                           │
└─────────────────────────────────────────────────────────┘
                             │
                             ▼
┌─────────────────────────────────────────────────────────┐
│  DETERMINING WHETHER A CURRENT AND/OR A PREDICTED       │
│  STATE OF THE USER IS WITHIN THE SAFE ZONE OR A         │
│  DANGER ZONE OUTSIDE THE SAFE ZONE                      │
│                           320                           │
└─────────────────────────────────────────────────────────┘
```

*Fig. 4*

UNIVERSAL MOBILE ALERT SYSTEM AND METHOD

CROSS REFERENCE TO RELATED APPLICATION

This application claims priority to U.S. provisional patent application No. 63/470,116 filed May 31, 2023, the contents of which are incorporated herein by reference in their entirety as if set forth verbatim.

FIELD

The present application relates to a personal universal mobile alert system and/or method.

BACKGROUND

Following an emergency, such as a medical emergency, one of the most important factors in determining whether a subject will survive is the time it takes for emergency medical services to be alerted and provide initial treatment. This critical period is known throughout as the "Golden Hour." In general, the sooner a subject receives care, the more likely the subject will survive. Additionally, even if the subject survives, any delay in initial treatment could result in reduced long-term quality of life (e.g., the subject is more likely to suffer lifelong disabilities).

Previous approaches to facilitate coordination between users and first responders have included devices, such as alert medallions, that require the user to push an alert or alarm button. Upon pushing the button, the user must typically wait and receive loud message(s) to wait as the alarm request is processing. Frustratingly, wait times in such previous approaches waste previous time especially as alarm operators handle other alarms during busy times. In processing alarm requests, alarm operators must also ask users to describe what kind of health problem they are experiencing which further wastes the precious time for providing help to the user and creates additional workload for alarm operators.

Often, the user's condition exasperates this problem since they commonly are physically unable to alert emergency medical services. There are many medical conditions that physically prevent a subject from personally contacting emergency medical services such as heart attacks, strokes, or complications from diabetes among others. For example, if a subject suffers a stroke they may be rendered unconscious, or at the very least paralyzed, and unable to call or alert others that they are in need of help. The subject's life would essentially rest on the chance that another person notices that the subject is in need of medical care with enough time to alert emergency medical services. As a result, there are many documented cases of subjects dying because there was no one around to notice that they were suffering a major medical emergency.

It is with respect to these and other considerations that the various embodiments described below are presented.

SUMMARY

Introduction/Digest to 2023 Patent Summary

PUMAS is invention of Personal Universal Mobile Medical, Police and Fire Security Emergency Alarm system working as a standalone Personal Universal Mobile Alert Security system or can be combined with Smart Phone for Medical intervention for quickest possible help to personal clients/population by local Medical, Police and Fire departments through local Regional Rapid Response Center (RCC), local hospitals, private medical centers, doctors, local medical institutions in case of life dangerous and critical situations.

PUMAS—Emergency Alert connectivity:

PUMAS is the Personal Universal Medical, Police and Fire Security Emergency Alarm System, monitoring 24/7/365 personal clients vital signs as a standalone independent system or wirelessly combined with any standard Smart Phone providing PUMAS personal users with quickest possible Emergency Alarm response and help by local Medical, Police and Fire local departments through Regional Rapid Response Centers in case of life critical and dangerous emergency situations.

PUMAS is part of Personal Area Network (PAN) and works nationwide on USA Mobile Virtual Network Operators (MVNOs)—three major cellular carriers: AT&T Mobility, T-Mobile US, and Verizon, as well as the regional carriers such as US cellular. As of 2016, MVNOs across the nation such as Metro by T-Mobile, Boost Mobile, Cricket Wireless, and Tracfone brands including Straight Talk have served about 36 million subscribers, cellular network, other USA national and on International cellular networks.

PUMAS service will cover USA, Canada and South American countries.

PUMAS will be modified for the rest of the world's continents/territories cellular network communication.

PUMAS direct clients and business partners are Emergency Alert companies, who are between individual users and Rapid Response Centers.

Individual users are potential direct clients of Emergency Alert companies.

Individual users are potential indirect clients of PUMAS Business project.

Personal and medical information of users/clients is protected by USA law.

Leakage/dissemination of personal and medical information of clients is civil and, in many cases, criminal violation punishable by heavy fines and class actions against violating entities.

All contracts with medical, business and law institutions require the user's permission to limits where and how to use personal user's information.

Emergency Alert companies, to protect personal and medical information of individual users, created their own specific RF 2-way encrypted, enciphered communication channel between user and Emergency Alert operator—single point/user to single point/operator encrypted RF line. Emergency Alert basic units, bracelets and medallion devices are designed with this specific RF 2-way encrypted Medical Alert channel for informational transfer between user and operator, one point to one point.

This 2-way channel is protected from smart phone channels.

This is the Platform of Emergency Alert companies, imposed on all Emergency Alert devices.

Therefore, any new universal PLATFORM cannot work with Emergency Alert companies.

PUMAS can be accepted by Emergency Alert partners only on the basis of encrypted Emergency Alert specific Platform.

The same requirements are imposed by Police and Fire Emergency Alert 2-way RF communication channels between user and operator.

All PUMAS devices are technologically 100% compatible ("talk with") with all Emergency Alert systems on today USA market, protecting client's private information.

Comparison of presently available on market the simplified Mobile Medical Alert technology and PUMAS technology:

Presently available simplified Mobile Medical Alert Basic devices for local private clients are wirelessly connected with local Rapid Response Center (RRC).

Basic device has clients personal RF Radio Beacon transmitter to locate client's location.

Local Rapid Response Center has client's name, address, 2-way wireless loud communication with client, contacts with local Medical Emergency centers/teems, names and phones of relatives to inform in case of Medical Alert case.

In order to get Medical Emergency help, client has to push Alarm push button of mobile Basic device, respond to questions of local RRC operator and ask for help.

The cost of the service provided to client by Medical Alert company is on average $35/month/$420/year, early contract subscription.

Fundamental problems of this technology:

It does not 24/7/365 continuously monitor the basic Vital Signs of client and does not respond automatically when client's Vital Signs are approaching Danger Red Zones.

When client push button, he is receiving loud message that he has to wait first for his Alarm request is processing, when wait available local Alarm Operator will contact client (delay "due to heavy work load"), finally available Alert operator request client to repeat his name and address, and then Alarm Operator is asking client to describe what kind of health problem client is experiencing—this process is wasting the precious time for providing help to client and creates additional workload for Alarm operators.

There is no feedback from medical office to intervene wirelessly in case of Danger Red Zones when client sleeping, unconscious or in diabetic coma, or for any other cases is unable to push Alarm push button, when the majority of Medical Alarm cases with morbidity, disability and mortality are the most frequent (up to 92%).

Doctors call the first hour to provide medical help in case of heart attack, stroke, diabetes emergencies as a "golden hour", greatly decreasing (up to 92%) the mortality and disability rate. In case of Police and Fire Alert emergencies it could be "golden minutes".

This technology does not provide the remote wireless intervention by medical office to adjust some parameters of current Vital Signs, adjust imbedded devises (for example, heart rhythm of pacemaker), detection of *Cannabis* or Alcohol intoxication, Air condition and blood poisoning.

Major advantages of PUMAS Medical Alarm technology/devices compared to present days simplified Medical Alert technology/devices:

PUMAS solves all fundamental problems of present-day Medical Alert technology, provides instantly valuable client's current Vital Signs information, greatly decreasing (up to 92%) the morbidity, mortality and disability rate, decreasing very significantly the workload for Alert Operators and saving Health Care cost in total.

PUMAS Major Points:
1) To combine Mobile Medical, Police and Fire Emergency Alert into Wearable Personal Universal Mobile Alert System (PUMAS) wirelessly connected to local Medical, Police and Fire Emergency departments, local hospitals, private medical centers, doctors, local medical institutions through Regional Rapid Response Centers and provide customers with quickest possible Emergency intervention and help.

The Mobile Emergency Alert Devices combines GPS (Global Positioning Satellite) and cellular (GPS ground Cell Tower) technology, enabling Rapid Response monitoring Center to be notified of exact mobile client location and establish 2-way communication of client with local Rapid Response Centers, local hospitals, private medical centers, doctors, local medical institutions.

2) If PUMAS client is unable to push Alarm button, or is client sleeping, or in coma, or unconscious or for any other reason unable to speak and some of his Life Vital Signs current approaching Danger Red Zones, the Alarm operator has instantly on his display all client's private and medical information and immediately can take steps to provide help to client—without delay of precious time and without unnecessary precious time consuming "high workload".

To provide local Medical, Police and Fire Emergency teams through Regional Rapid Response Centers with client's life critical Medical Emergency information when Emergency Alarm signal is initiated by client to minimize response delay for quick intervention and help:

When the client is pressing the PUMAS Alarm push button, the PUMAS mobile device will provide 2-way voice contact with local Rapid Response emergency monitoring center.

If the client is silent and incapable for one minute to respond to Rapid Response Center after Alarm signal initiated, local Rapid Response Center automatically connects client location and his current Vital Signs information with local Medical, Police and Fire Emergency teams for quickest possible response and sends local Emergency teams to provide immediate help to client. The Emergency Team and Hospital Emergency Department have instantly clients current Vital Signs on screen.

If a personal client's Vital Signs are approaching the Vital Signs Red Danger zone and client does not initiate Alarm Signal push button, PUMAS automatically contacts local Rapid Response Center with client's current Vital Signs information to send Emergency Team to provide the help to client.

Accuracy of PUMAS Mobile GPS location is calculated by receiving direct Satellite GPS signals and does not depend on Cell Towers territorial distribution.

The new G5 technological standard provides clients with 10 feet mobile accuracy location in Emergency situation.

3) To provide continuous 7/24/365 monitoring, automatic intervention, feedback medical correction to PUMAS by medical office and help in case of Medical Vital Signs Red Line Life Danger and Geofencing crossing.

PUMAS Technology

All PUMAS category devices have capacity for customized personal RF programming, providing auto intelligent feedback correction of client's medical condition as a reaction on client's current medical Vital Signs, approaching Life Danger Red Lines borders by PUMAS continuous 24/7/365 monitoring of client's current Vital Signs, Police and Fire alarms.

The standard set of PUMAS technology is NOT meant for FDA regulated diagnostic applications of critical Vital Signs conditions.

Future PUMAS sets can be under FDA regulated diagnostic applications of critical Vital Signs conditions.

Additional Modification of Special PUMAS Wearable Wireless unit, Pendant/Medallion or Wrist device is to control Substance and Alcohol Abuse by Police and Fire departments and DMV.

Additional Modification of Personal Remote Wearable Wireless Geo Fencing unit, Pendant/Medallion or Wrist device is for the children Parental Control and Security/Protection.

Additional Modifications of Personal Remote Wearable Wireless units are possible for new bio sensitive sensors and medical conditions.

PUMAS Wearable Wireless bio sensitive patch can be placed on human skin at any place of human body.

All PUMAS devices have client's personal RF Radio Beacon transmitter to locate client's mobile location with GPS accuracy.

A Wearable Medical Alert electronic Tag/Emblem, a client's dangerous personal life chronic conditions to instantly alert Emergency Team and Doctors, incorporated into all PUMAS devices (Wrist, Basic units and Pendants/medallion/Wrist pushbutton), bearing a message that the wearer has an important medical condition that might require immediate attention. For emergency medical providers such as paramedics and emergency physicians, medical identification tags are particularly useful in situations where the wearer is unconscious, altered mental status, very young, or otherwise unable to provide critical medical information.

A type of medical identification alert is the USB and Wireless Wearable Medical Alert tag, essentially a USB flash drive with capacity to store a great deal of emergency information, including contacts and serious medical conditions. This Medical Alert information, in accordance with patient's personal health chronic conditions, mandatory installed by blue tooth or smart phone into all PUMAS devices and be accessible by any computer wirelessly or with a USB port at PUMAS Basic device.

It should be protected from malware. The tag wirelessly incorporated into PUMAS should 100% belong to legal PUMAS client, excluding medical staff from risks to health and legal liability of medical personnel if device is carried by an unconscious person may not be their own.

Additional new type of personal Medical Identification Alert is QR code based Medical Alert installed at all PUMAS devices. The QR code on the PUMAS links to a web service that contains the individual's emergency information. The information is accessed by any first Responder or Emergency personnel by scanning the QR code by using a smartphone or PUMAS devices. In addition to QR codes in all PUMAS devices included an embedded RFID chip that allows a first responder to simply tap their smart phone against the device. Since a web service is used to store the information in cloud, there is normally no limitation on how much information can be stored.

Examples of Medical Conditions electronic tags installed in PUMAS and using typical conditions and prescriptions warranting. The wearing of such a tag includes but are not limited to:

Allergies
Adrenal insufficiency
Advance Medical Directives (Do Not Resuscitate, POLST, Lasting Power of Attorney, Living Will)
Anaphylaxis allergies (food, drug, insect)
Alzheimer's disease[2]
Angioedema (hereditary)
Anemia[3]
Asthma
Asplenia
Autism[4]
Cerebrovascular incident[5]
Chemotherapy
Blood type (rare)
Dementia
Diabetic (Type 1 and 2)
Epilepsy
Hemodialysis
Hemophilia
Hypoglycemia
Hypopituitarism
Lamotrigine
Drug-induced Long-QT syndrome
Lymphedema risk
Use of a monoamine oxidase inhibitor (MAOI) drug, which can interact fatally with epinephrine
Memory disorders
Pacemaker or other implantable medical devices
Porphyria (acute)
Seizure disorders
Situs inversus
Von Willebrand Disease
Plus over 100+ autoimmune diseases, including disorders
Anxiety
Parkinson's disease
Alzheimer's disease
Dementia
Multiple sclerosis
Epilepsy
Autism spectrum disorder
Depression
Anxiety Plus over 100+ autoimmune diseases, including:
Disorders
Bipolar disorder
Hepatic encephalopathy
Neuropathic pain
And more
It will allow the first medical responder, Emergency operators and doctors to avoid deadly mistakes.
All client's medical information will be instantly on screen to all Medical Alert responders.

PUMAS provides:
Electronic Health Records Recording and Archiving, Patent Personal Portals, Patent's Self-Monitoring, Early Disease Detection/Diagnostic, enables to Sense, Reason, Adapt and Correct client's Vital Signs information by clinicians, decreasing work load of Medical Alert operators and Emergency team, reduce the overall Health Care cost through 24/7/365 monitoring and automatic intervention into personal human life Vital Signs approaching danger Red Zones, decreasing (up to 92%) the mortality, morbidity and disability rate in case of Medical, Police and Fire Alert Emergencies.

Presently available WEARABLE WIRELESS biomedical customized Vital Signs sensors for PUMAS applications:

Heart:
Heart Rhythm •Heart Rhythm Variability •Stress •Personalization •Heart Rate Training Zone •Heart Rate Recovery •Respiration Rate •More under development
ECG (electrocardiogram)
PC (heart pacemaker) remote wireless adjustment by medical office to patient through PUMAS.
Heart attack detection
Arrythmia: Atrial FIB and Ventricular FIB
Blood Glucose monitoring for remote diabetes management/coma prevention.

Blood Oxygen

Blood Pressure (plastic smart bio sensitive band)

Wearable sensors guide Precision Remote Drug Dosing from medical office to patient through POMAS.

Body Impedance (body poison remote wireless diagnostic)

Anemia

Dehydration

Chronic wound monitoring

*Cannabis* intoxication detection

Air contamination measurement

The changing of tumors size below the skin

Real-time, wearable wireless, continuous Auscultation to record and visualize modern auscultation (lunq and heart diaqnostic), to automate diagnoses of four types of disease in the lung, ranging from a crackle, to a wheeze, stridor and rhonchi, with 95% accuracy. The soft system is applicable for a sleep study to detect disordered breathing and to detect sleep apnea. Chronic obstructive pulmonary disease (COPD) and cardiovascular disease (CVD) are predominant factors of mortality worldwide.

Chronic obstructive pulmonary disease (COPD) and cardiovascular disease (CVD) are predominant factors of mortality worldwide. Accurate auscultation is helpful to diagnose disease at an early stage and evaluate the treatment response. Similarly, heart sounds also facilitate diagnosis and the identification of vascular heart diseases.

Wearable Wireless Infrared Body Temperature

All/New future biomedical wearable wireless Vital Signs sensors, coming on the market and applicable for 24/7/365 Monitoring, Diagnostic and Intervention by clinicians through PUMAS.

PUMAS Standard set,

Personal Universal Mobile Alert Security System (PUMAS) has 3 Wearable Mobile devices:

1)

Wearable Mobile Basic PUMAS device can work as standalone independent device to provide all PUMAS services or to be combined with standard Smart Phones into one Personal Universal Mobile Alert 24/7/365 System by Incorporating PUMAS into standard Smart Phone casing mechanically (by magnetic bar) with Bluetooth connectivity for recording and retransmitting of client's static and mobile personal data by Smart Phone.

No changes to the smart phone itself.

Wearable Mobile Basic PUMAS device can work as independent standalone wearable mobile unit, having all PUMAS functions:

Direct Satellite Transponder for exact GPS calculations of client's mobile locations, client's static and mobile personal data, client's personalized current primary and secondary Vital Signs information, Exact Location Radio Beacon, Two-Way RF channel for client to communicate with Rapid Response Center, RF transponder for automatic intervention for continuous monitoring, correction and help in case of Medical Vital Signs Red Line Life Danger and Geofencing danger area crossing.

2)

Wearable mobile waterproofed Wrist Bracelet with GPS exact location transponder, primary and secondary Vital Signs sensors with customized medical and/or fitness accuracy, Bluetooth and Wi-Fi connectivity, RF long distance transponder to Basic PUMAS device and to Regional Rapid Response Center.

User will set/customize in medical office his personal vital signs and the medical Life Danger Red Lines with medical level accuracy and set for Rapid Response Border Intervention when user is unable to push Emergency Alert button or incapable of speaking with Rapid Response Center.

PUMAS Emergency Alarm push button will send to Rapid Response Medical Center the Emergency Alarm with patient's static and mobile current Vital Signs information for local Medical, Police and Fire departments emergency teams.

Emergency teams will have patient's static and current Vital Signs information on the way to patient and do not need to spent time by taking Vital Signs at patient's location.

The Medical Emergency team will provide the patient's current Vital Signs information in advance to an appropriate hospital emergency department.

Medical Rapid Response Center will have patient's static personal information: patient's ID, address, prescribed medications, group of blood, allergy information, patient's doctor and hospital and relative's names and phone numbers and mobile current Vital Signs information with Life Danger Red Lines limits.

Police/Fire Rapid Response Center will have patient's personal ID, address and more information set by client himself, including medical information.

He can add his personal medical information—it could be helpful in case of emergency.

The emergency team on the way to the patient will already have the personal Vital Signs of patient and send this information to hospital team specialized in emergency care of patient with such Vital Signs.

It will greatly reduce the delay time of medical intervention in hospital, providing medical help to patient during so-called (by doctors!) "golden" hour.

Doctors call the first hour to provide medical help in case of heart attack, stroke, diabetes emergencies as a "golden hour", greatly decreasing (up to 92%) the mortality and disability rate. In case of Police and Fire Alert emergencies it could be "golden minutes".

The PUMAS units should be powered independently by thin film lithium battery up to 72 operational hours per charge (or more).

3)

PUMAS Wearable mobile Neck Pendant/Medallion or waterproofed Wrist pushbutton with its own mobile GPS location transmitter, continuous GPS monitoring and retransmitting of GPS exact location signal (G5 Standard, 10 feet accuracy) with transmission distance to PUMAS Basic at least distance of 200 feet:

PUMAS Personal Radio Beacon/Radio Medallion (transmission distance depending on power battery):

Configured as pendant, or medallion in pocket, or in purse, etc. to be a Personal Transmitter of RF Emergency Alert location in case of no response from client, when Emergency Alert signal initiated by Smart Phone or Wrist Bracelet Transponders.

Personal Beacon/Radio Pendant/Medallion and Wrist pushbutton has battery and GPS location chipset with transmitter of Emergency Location RF signal for at least 12 or more hours.

Wearable Waterproof Neck Pendant/Medallion or Wrist pushbutton Circuitry:

RF Power Supply

RF Micro-Antenna

PUMAS biomedical patch/contact can be placed on the surface on human skin.

Pumas Setting:

Setting of mobile GPS tracking and geographic boundaries locations (geofencing) with Alarm notification (to be notified by Smart Phone if the geofencing perimeter is violated).

Bluetooth setting for static basic Vital Signs information recording.

Bluetooth setting for:

Personalized customized setting of personal Vital Signs

Sound Auto Reminder for taking medications.

Emergency Alarm Micro Push Button

Personal RF Radio Beacon transmitter of Emergency Exact Location and basic information set of static customized Vital Signal information.

RF Emergency Alarm 2-way WI-FI transponder with Smart Phone through local cell Towers activated by Alarm Emergency signal.

Laud Siren activated by Emergency push button.

Alarm Emergency Video activated by Emergency Alert signals.

PUMAS Vital Signs and Medical Alert information in Mobile Basic PUMAS System:

PUMAS Medical Alert set of personal Vital Signs will be customized for each client (through Bluetooth setting) in medical office.

Specific Life Danger Red Line limits of Vital Signs will be customized for each client (depending on heart, lung, blood sugar, etc., chronic health problems):

Critical Vital Signs readings, approaching specific Life Danger red lines limits, will start visible and sound Alarm signals on PUMAS Mobile Basic device, on PUMAS Smart Wrist bracelet display:

Rapid Response Center initiates the Rapid Response Help Intervention if client does not respond during 45 seconds after push button initiating of Medical or Police/Fire Emergency loud signal.

PUMAS Police/Fire Emergency Alarm channel will have client's personal, medical static and medical mobile information.

Patient's Personal Static Information:

Patient's personal PUMAS ID, address, phone, email, medications, group of blood, patient's doctor, patient's hospital, patient's personal Vital Signs Red Line Life Danger limits information, names/phones to contact in case of Emergency;

Patient's personal mobile information:

Patient's personal static information plus patient's mobile current Vital Signs information from Pumas Wrist Bracelet.

Basic Primary Personal Desirable Minimal Meagerable Vital Signs listing:

Heart Rhythm

Heart Variable Rate

Oxygen Saturation Rate/Pulse Oximetry

ECG (ELECTOGARDIOGRAM)

AFIB and VFIB

Blood Pressure (indirect estimation by wrist bracelet sensor information)

Blood Glucose/Sugar

Anemia

Life Danger Red Line limits of Vital Signs

Falling Alarm Sensors

Secondary Desirable Meagerable Vital Signs Listing:

EEG (ELECTROENCEPHALOGRAPHY)

EMG (ELECTROMYOGRAPHY, electrical potential generated by muscle by neurologically activated)

Skin temperature and body impedance

Skin conductance (detect poison for unconscious patient)

Body impedance

Gait Speed

Environmental Danger signals:

Carbon Dioxide, Smoke, PM2.5 and PM10 (2.5 microns and 10 microns most dangerous pollutants)

Volatile Organic Compounds/Allergenic (VOC)

Bio sensor on skin surface of mosquito-borne viruses for early very critical medical intervention Leg diameter/swelling Area Perimeter crossing lines (Geofencing)

Alarm Emergency Video activated by Emergency Alert signals

Alarm Emergency Sound Siren

PUMAS Measurable Vital Sings have potential for calculation of not measurable at present time Vital Signs Any new Wireless Wearable biomedical life Vital Signals on coming on market.

PUMAS Telemedicine applications:

PUMAs uses the telecommunication and information technology to provide remote Clinical Health care from a distance.

Telemedicine is to overcome distance barriers and to improve access to medical services that would often not be consistently available in distant rural communities. It saves lives in Critical Care, Medical, Police, Fire, Earthquake Emergency Situations and in Remote Advanced Diagnostic Methods supported by distributed client/server applications to local medical centers.

PUMAS have real-time capacity for prediction for flu and infectious diseases.

PUMAS Tele-epidemiology applies satellite communication systems to investigate and support investigations of world infectious disease outbreak, including disease reemergence. In this application, PUMAS use the natural index and in-situ data (i.e. NDVI, Meteosat, Envisat) to assess health risk to human and animal populations. Space-based applications of tele-epidemiology extend to health surveillance and health emergency response in case of epidemic. Pumas technologies permit communications between patient and medical staff with both convenience and fidelity, as well as the transmission of medical, imaging and health informatics data from one site to another.

PUMAS Benefits and Applications

Telemedicine is beneficial to users in isolated communities and remote regions, who can receive care from doctors or specialists far away without the patient having to travel to visit them. Mobile Collaboration technology allow healthcare professionals in multiple locations to share information and discuss patient issues as if they were in the same place. Remote patient monitoring through Mobile Technology can reduce the need for outpatient visits and enable remote prescription verification and drug administration oversight, potentially significantly reducing the overall cost of medical care.

Almost two thirds of thoracic oncologists used telehealth for the first-time during pandemic.

PUMAS Telemedicine also facilitates medical education by allowing workers to observe experts in their fields and share best practices more easily. Telemedicine eliminates the possible transmission of infectious diseases or parasites between patients and medical staff.

PUMAS Market Base, Financial and Possible Profit Aspects:

Reductions in the cost of providing quality care to the chronically ill, estimated by the Center for Health Care Economics at the Milken Institute, exceeded $1.3 trillion just in USA alone per year in 2014 and is growing every year. In 2017 there were over 77 million senior citizens just in the USA and this number is growing every year.

Health Care costs will take over 18% of USA GDP in 2023, 2 times more than the Defense budget.

American Medical Association (AMA) estimated, that at least 50% of USA population now has at least one chronic debilitating disease and some have multiple such illnesses.

Add to these potential PUMAS users the workers of Construction, Agricultural, Transportation industries, Police and Fire Departments, private medical offices, Alarm Emergency demands in case of pandemic, fire and earthquake emergencies.

We are receiving an enthusiastic response from all potential PUMAS clients.

Before we introduce PUMAS in the USA market, already in some states the administrations, realizing Health Care saving, began to allocate state budget money to pay private clients for old simplified "push button" Medical Alert services.

PUMAS direct clients and business partners are Emergency Alert companies, who are between individual users and Rapid Response Centers.

Individual users are potential direct clients of Emergency Alert companies.

Individual users are potential indirect clients of PUMAS Business project.

PUMAS technology and wearable wireless service is the perfect instrument to generate consumable, from year to year, revenue for high quality PUMAS Medical Alert service and overall Health Care savings to state and country.

2023 Snell & Wilmer Patent Summary

Embodiments of the present disclosure include a system and method that provides continuous health monitoring of user and coordination of an automatic alert to a first responder(s) when care is needed.

In some aspects, a system is disclosed for monitoring a user and coordinating one or more alert response by one or more first responders and configured to connect to one or more monitoring devices. The system includes a mobile device configured to perform operations. The operations include obtain user data from a continuous user data stream from the one or more monitoring devices; determine, based on the user data stream and user historical records, a safe zone of the user; and determine, based on a user data stream and user historical records, whether a current state or a predicted state of the user is within the safe zone and/or a danger zone defined as being outside the safe zone.

In some aspects, the operations include analyze the user data stream based on defined parameters of the safe zone related to the user; and alert the user and/or the one or more first responders when the data or information is outside the safe zone.

In some aspects, the first responder includes one or more first responders including law enforcement, fire protection, ambulance, security guards, or other personnel.

In some aspects, if the user is not within the safe zone and/or is within the danger zone, then transmit to the one or more first responders one or more monitoring device generated diagnostics, user medical records, imaging records, previous doctor's assessment and/or intervention(s), user health informatics data records, and/or a geographical location of the user.

In some aspects, if the user is not within the safe zone and/or is within the danger zone, then automatically establish, by the one or more monitoring devices, 2-way communication between the user and the one or more first responders.

In some aspects, if the user fails to respond to the alert within a predetermined period of time, then transmit, by the one or more monitoring devices and/or a user computing device, an emergency alert signal to the one or more first responders.

In some aspects, the operations include receive, from the first responder, a response to the alert, wherein the first responder includes at least a rapid response center configured to coordinate one or more response with a law enforcement department, a fire department, a hospital, a private medical center, a doctor, a neighbor, and/or an emergency contact of the user.

In some aspects, the operations include apply a machine learning model to generate one or more predictions of the safe zone and/or the danger zone of the user based on a zone criteria presence of the user data, the one or more predictions comprising a binary output to indicate a plurality of relevant diagnostic features based on medical metadata of the user data, the machine learning model having been developed using the continuous user data stream, archived user data, and prospective user data.

In some aspects, the vital signs considered in determining user specific zones, determining and/or predicting user states, and/or zone classification include heart rate, heart variable rate, oxygen saturation rate, pulse oximetry, electrocardiogram (ECG), breathing rate, blood pressure, heart arrhythmia, blood glucose, physiological boundary limits, physically falling, electroencephalography (EEG), electromyography (EMG), skin temperature, blood alcohol, other substance levels in blood, body impedance, skin conductance, loss of blood, loss of plasma, loss of blood sodium, changes in the diameter of the individuals extremities, and/or gait speed.

In some aspects, the vital signs considered in determining user specific zones, determining and/or predicting user states, and/or zone classification include Adrenal insufficiency, Advance Medical Directives, Anaphylaxis allergies, Alzheimer's disease, Angioedema, Anemia, Asthma, Asplenia, Autism, Cerebrovascular incident, Chemotherapy, Blood type (rare), Dementia, Diabetic (Type 1 and 2), Epilepsy, Hemodialysis, Hemophilia, Hypoglycemia, Hypopituitarism, Lamotrigine, Drug-induced Long-QT syndrome, Lymphedema risk, Use of a monoamine oxidase inhibitor (MAOI) drug, which can interact fatally with epinephrine, Memory disorders, Pacemaker or other implantable medical devices, Porphyria (acute), Seizure disorders, Situs inversus, and/or Von Willebrand Disease.

In some aspects, the one or more monitoring devices include a heart monitor, a watch, a pulse monitor, a glucose sensor, a smartphone, a wrist bracelet, a ring, a medallion, a pendant, and/or a smartphone case, and wherein the one or more monitoring devices at least comprise a rechargeable battery, memory, and a transponder to bidirectionally communicate with one or more external computing devices.

In some aspects, one or more boundaries of the safe zone, an intermediate zone, and/or the danger zone of the user are not editable by the user.

In some aspects, the operations include generate the user data stream based on data from one or more sensors of the one or more monitoring devices, the one or more sensors being configured to detect vital signs and/or location associated with the user, the one or more monitoring devices comprising a wearable device wearable by the user and/or a mobile computing device.

In some aspects, the safe zone is determined by determining, based on location data of the user data stream, when the user is located within a predetermined geographical area;

and generating an alert that the user is no longer in the safe zone and/or is in the danger zone when the user is detected as being located outside the predetermined geographical area.

In some aspects, the one or more monitoring devices include a wearable device donned by the user, and wherein a location of the user is determined using a radio frequency (RF) beacon coupled to the wearable device donned by the user. The wearable device can be a wrist bracelet, a tag, a ring, a medallion, a garment, and/or a pendant.

In some aspects, the operations include transmit the user data stream to at least one of a cloud, a server, and/or another device.

In some aspects, a method is disclosed for monitoring a user and coordinating one or more alert response by one or more first responders. The method includes obtaining, by the processor, user data from a user data stream from the one or more monitoring devices; determine, by the processor and based on the user data stream and user historical records, a safe zone of the user; and determine, by the processor and based on a user data stream and user historical records, whether a current state or a predicted state of the user is within the safe zone and/or a danger zone defined as being outside the safe zone.

In some aspects, the method includes analyzing, by the processor, the user data stream based on defined parameters of the safe zone related to the user; and alerting, by the processor, the user and/or a third party when the data or information is outside the safe zone.

In some aspects, one or more boundaries of the safe zone, an intermediate zone, and/or the danger zone of the user are not editable by the user.

In some aspects, the method includes generating the user data stream based on data from one or more sensors of the one or more monitoring devices, the one or more sensors detecting vital signs and/or location associated with the user, the one or more monitoring devices including a wearable device wearable by the user and/or a mobile computing device.

In some aspects, the method includes if the user is not within the safe zone and/or is within the danger zone, then transmitting to the one or more first responders one or more monitoring device generated diagnostics, user medical records, imaging records, previous doctor's assessment and/or intervention(s), user health informatics data records, and/or a geographical location of the user.

In some aspects, the method includes if the user is not within the safe zone and/or is within the danger zone, then automatically establishing, by the one or more monitoring devices, 2-way communication between the user and the one or more first responders.

In some aspects, the method includes if the user fails to respond to the alert within a predetermined period of time, then transmitting, by the one or more monitoring devices and/or a user computing device, an emergency alert signal to the one or more first responders.

In some aspects, a personal universal mobile alert system is disclosed for monitoring an individual and providing valuable information to the individual and/or a third party responder (e.g., a police department, a fire department, medical personnel, a friend, and/or other persons or systems concerning the location, health, safety or other information of the individual in case of dangerous life and other critical situations).

In some aspects, through the use of the herein disclosed system, critical user information is obtained and communicated including the location, health, safety, and other information about the user or individual.

In some aspects, the herein disclosed system is configured to assist the user by notifying the user and/or medical personnel if user biometrics within a danger zone (e.g., user's heart rate, blood pressure is outside an acceptable range, a fall by the user has been detected, etc.). In some aspects, the danger zone can be understood as simply being outside a safe zone of the baser, based on both historical patient data streams, whereby the safe zone is defined by patient health levels being considered safe. In some aspects, an intermediate zone is determined based on an indication to a patient that one or more health levels are within a warning range that is close to being outside or just the limit of the safe zone.

In some aspects, the danger zone is detected if the user has travelled outside a confined area during a hike or a walk. Upon detecting presence of the danger zone, the system can notify the user, one or more first responders (e.g., the police, the fire department, etc.), and/or a trusted family member (e.g., a parent). In some aspects, if the user is a child and the child has been detected as being in the danger zone by having travelled outside the safe zone (e.g., outside the house or the backyard), the system can automatically call the third party responders (e.g., the police, the fire department, medical personnel, etc.). In some aspects, users of the system can be young active children, adults, senior citizens, disabled individuals, law enforcement personnel, fire protection personnel, emergency medical personnel, hikers, skiers, hunters, field workers, long distance truck drivers, coastal area boat personnel, among others.

In some aspects, the system is a universal system that receives information from one or more monitoring or location devices (e.g., a wearable vital signs monitor) and provides automatic alerts, notifications, and/or related information to the user and/or third party responders. In some aspects, the wearable vital signs monitor can transmit continuous physiological data stream of a user and/or synchronized with the historical patient data streams, resulting not only in improved health but also safety of the user.

In some aspects, the system also provides an additional level of safety sending an automatic alert to third party responders when one or more values of the user health information is outside or approaching being outside the safe zone (e.g., the user is sleeping, in a coma, and/or unable to speak or otherwise communicate for any other reason to use alarm push button). In some aspects, if user health information (e.g., vital signs of the user) enters the danger zone and/or the user is unable to respond to a rapid response team, the system automatically notifies one or more third party responders (e.g., rapid response team in case of medical, police or fire life danger emergency). In turn, delays are shortened and response times of emergency responders are improved. In some aspects, if the system detects that the user has not moved (e.g., moved from one location to another, is not breathing, has fallen, etc.) for a period of time (e.g., 45 seconds), an emergency alert is automatically sent to one or more third party responders.

In some aspects, the system may utilize geofencing to determine whether a user is within the danger zone so as to notify and respond to potential emergencies. As used herein, the term "geofence" and/or "geofencing" means a virtual perimeter of the geographic area and can be dynamically generated or match a predefined set of boundaries. For example, the system can determine if a user is within a predefined geofenced area and if outside the defined geofence area then the system will automatically notify one or more third party responders as well as the user that the user is within the danger zone so that appropriate action can take place. In certain cases, this geofence area is defined using one or more of geofencing technology, GPS coordinates, and/or a distance from this defined area. In some aspects, the geofence utilized outlines a permissible geographical area and a dangerous geographical area outside the permissible geographical area. In some aspects, if the user ventures outside of the permissible geographical area into the dangerous geographical area, the system can determine that the user is in the danger zone and transmit an automatic alert to third party responders (e.g., police, fire, child's parent, or other personnel). For example, a hiker may inadvertently stray off of a trail and get lost in the wilderness and the system can be configured to detect that the hiker is off the trail or lost (e.g., the hiker is in the danger zone). Accordingly, emergency response services may be automatically notified by the system when the user's location indicates that they have ventured into the dangerous geographical area.

In some aspects, a method is disclosed for a personal universal mobile alert system. The method includes obtaining a vital signs data stream associated with a user, analyzing the user data stream in real-time, determining a safe zone of the user based on user historical patient records, including but not limited to user medical records, imaging records, archived and/or doctor's assessment and/or intervention(s), health informatics data records, and the user data stream, and determining whether a current state of the user is within the safe zone or a danger zone outside the safe zone.

In some aspects, the method includes upon determining that the current state of the user is outside the safe zone and/or within the danger zone, transmitting an alert to one or more third party responders.

In some aspects, aspects of the herein disclosed system can be embodied in a mobile device, a system and/or apparatus for monitoring and transmitting alert notifications regarding a state of a user. In some aspects, the mobile device includes a memory that is configured to store an application. The mobile device can include one or more processors configured to perform operations of the application. The operations include obtaining a vital signs data stream associated with a user, analyzing the user data stream continuously in real-time, determining a safe zone of the user based on user historical patient records and the user data stream, and determining whether a current state of the user is within the safe zone or a danger zone outside the safe zone. The operations include upon determining that the current state of the user is outside the safe zone and/or within the danger zone, transmitting an alert to one or more third party responders.

In some aspects, the operations include receiving, from the one or more third party responders, a response to the transmitted alert. The operations may include transmitting, to the one or more third party responders, a geographical location of the user. The operations may include determining when the subject is located within a predetermined geographical area and generating an alert when the user is located outside the predetermined geographical area. The operations may include transmitting a location data stream associated with the user to at least one of a cloud, a server, or another device.

In some aspects, a geofence area defining a boundary limit of the user may not be editable by the user. In some aspects, a location of the subject may be determined using a radio frequency (RF) beacon coupled to the user.

Other aspects and features of the present disclosure will become apparent to those of ordinary skill in the art, upon reviewing the following detailed description in conjunction with the accompanying figures.

BRIEF DESCRIPTION OF THE FIGURES

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 4 is an example process implemented by a personal universal mobile alert system, according to an example embodiment.

DETAILED DESCRIPTION

Figure 1:
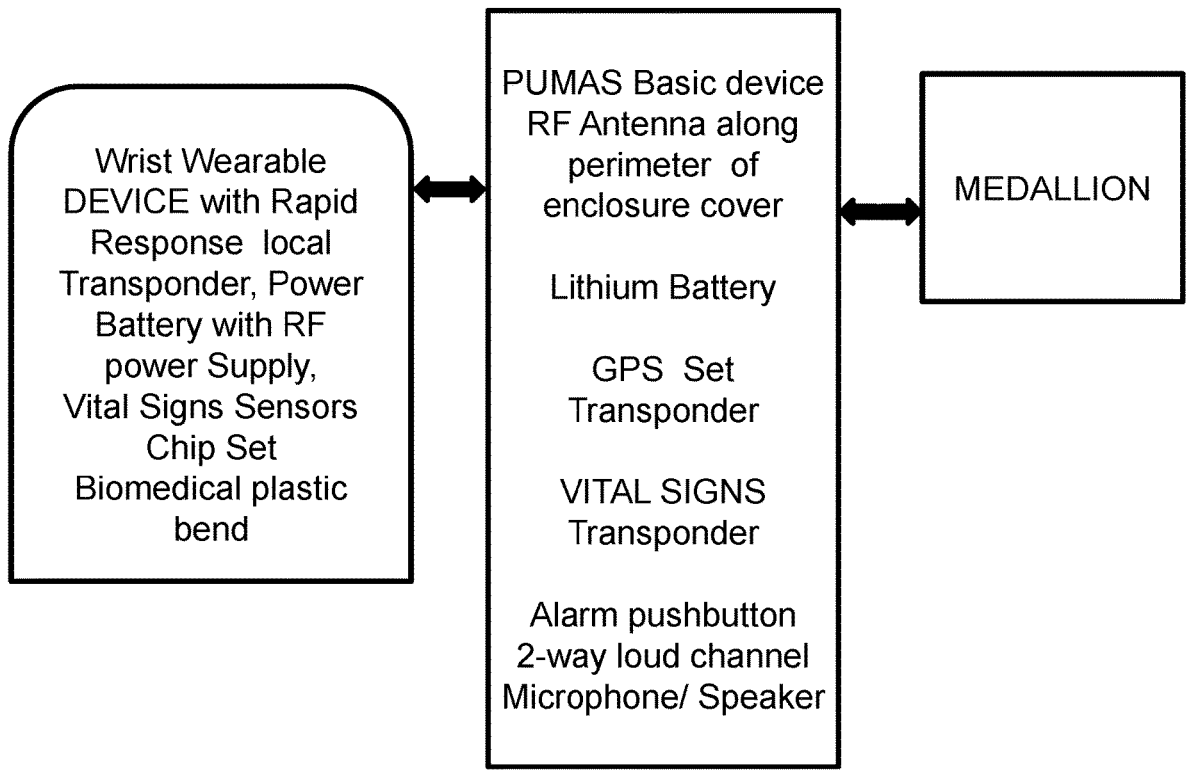
FIG. 1 illustrates an example block diagram of an example monitoring and alert system, according to an example embodiment.

This description provides examples, and is not intended to unnecessarily limit the scope, applicability or configuration of the solution of this disclosure. Rather, the ensuing description will provide those skilled in the art with an enabling description for implementing embodiments of the solution. Various changes may be made in the function and arrangement of elements. Thus, various embodiments may omit, substitute, and/or add various procedures or components as appropriate. For instance, aspects and elements described with respect to certain embodiments may be combined in various other embodiments. It should also be appreciated that the following systems, devices, and components may individually or collectively be components of a larger system, wherein other procedures may take precedence over or otherwise modify their application.

In some instances, a computing device may be referred to as a mobile device, mobile computing device, a mobile station (MS), terminal, cellular phone, cellular handset, personal digital assistant (PDA), smartphone, wireless phone, organizer, handheld computer, desktop computer, laptop computer, tablet computer, tablet, terminal, display device, or some other like terminology. In other instances, a computing device may be a processor, an electronic control unit (ECU), a controller, a server, or a central processing unit (CPU). In yet other instances, a computing device may be a set of hardware and software components.

Examples of the Invention

PUMAS is invention of Personal Universal Mobile Medical, Police and Fire Security Emergency Alarm system working as a standalone Personal Universal Mobile Alert Security system or can be combined with Smart Phone for Medical intervention for quickest possible help to personal clients/population by local Medical, Police and Fire departments through local Regional Rapid Response Center (RCC), local hospitals, private medical centers, doctors, local medical institutions in case of life dangerous and critical situations.

PUMAS—Emergency Alert connectivity:

PUMAS is the Personal Universal Medical, Police and Fire Security Emergency Alarm System, monitoring 24/7/365 personal clients vital signs as a standalone independent system or wirelessly combined with any standard Smart Phone providing PUMAS personal users with quickest possible Emergency Alarm response and help by local Medical, Police and Fire local departments through Regional Rapid Response Centers in case of life critical and dangerous emergency situations.

PUMAS is part of Personal Area Network (PAN) and works nationwide on USA Mobile Virtual Network Operators (MVNOs)—three major cellular carriers: AT&T Mobility, T-Mobile US, and Verizon, as well as the regional carriers such as US cellular. As of 2016, MVNOs across the nation such as Metro by T-Mobile, Boost Mobile, Cricket Wireless, and Tracfone brands including Straight Talk have served about 36 million subscribers, cellular network, other USA national and on International cellular networks.

PUMAS service will cover USA, Canada and South American countries.

PUMAS will be modified for the rest of the world's continents/territories cellular network communication.

PUMAS direct clients and business partners are Emergency Alert companies, who are between individual users and Rapid Response Centers.

Individual users are potential direct clients of Emergency Alert companies.

Individual users are potential indirect clients of PUMAS Business project.

Personal and medical information of users/clients is protected by USA law.

Leakage/dissemination of personal and medical information of clients is civil and, in many cases, criminal violation punishable by heavy fines and class actions against violating entities.

All contracts with medical, business and law institutions require the user's permission to limits where and how to use personal user's information.

Emergency Alert companies, to protect personal and medical information of individual users, created their own specific RF 2-way encrypted, enciphered communication channel between user and Emergency Alert operator—single point/user to single point/operator encrypted RF line. Emergency Alert basic units, bracelets and medallion devices are designed with this specific RF 2-way encrypted Medical Alert channel for informational transfer between user and operator, one point to one point.

This 2-way channel is protected from smart phone channels.

This is the Platform of Emergency Alert companies, imposed on all Emergency Alert devices.

Therefore, any new universal PLATFORM cannot work with Emergency Alert companies.

PUMAS can be accepted by Emergency Alert partners only on the basis of encrypted Emergency Alert specific Platform.

The same requirements are imposed by Police and Fire Emergency Alert 2-way RF communication channels between user and operator.

All PUMAS devices are technologically 100% compatible ("talk with") with all Emergency Alert systems on today USA market, protecting client's private information.

Comparison of presently available on market the simplified Mobile Medical Alert technology and PUMAS technology:

Presently available simplified Mobile Medical Alert Basic devices for local private clients are wirelessly connected with local Rapid Response Center (RRC).

Basic device has clients personal RF Radio Beacon transmitter to locate client's location.

Local Rapid Response Center has client's name, address, 2-way wireless loud communication with client, contacts with local Medical Emergency centers/teems, names and phones of relatives to inform in case of Medical Alert case.

In order to get Medical Emergency help, client has to push Alarm push button of mobile Basic device, respond to questions of local RRC operator and ask for help.

The cost of the service provided to client by Medical Alert company is on average $35/month/$420/year, early contract subscription.

Fundamental problems of this technology:

It does not 24/7/365 continuously monitor the basic Vital Signs of client and does not respond automatically when client's Vital Signs are approaching Danger Red Zones.

When client push button, he is receiving loud message that he has to wait first for his Alarm request is processing, when wait available local Alarm Operator will contact client (delay "due to heavy work load"), finally available Alert operator request client to repeat his name and address, and then Alarm Operator is asking client to describe what kind of health problem client is experiencing—this process is wasting the precious time for providing help to client and creates additional workload for Alarm operators.

There is no feedback from medical office to intervene wirelessly in case of Danger Red Zones when client sleeping, unconscious or in diabetic coma, or for any other cases is unable to push Alarm push button, when the majority of Medical Alarm cases with morbidity, disability and mortality are the most frequent (up to 92%).

Doctors call the first hour to provide medical help in case of heart attack, stroke, diabetes emergencies as a "golden hour", greatly decreasing (up to 92%) the mortality and disability rate. In case of Police and Fire Alert emergencies it could be "golden minutes".

This technology does not provide the remote wireless intervention by medical office to adjust some parameters of current Vital Signs, adjust imbedded devises (for example, heart rhythm of pacemaker), detection of *Cannabis* or Alcohol intoxication, Air condition and blood poisoning.

Major advantages of PUMAS Medical Alarm technology/devices compared to present days simplified Medical Alert technology/devices:

PUMAS solves all fundamental problems of present-day Medical Alert technology, provides instantly valuable client's current Vital Signs information, greatly decreasing (up to 92%) the morbidity, mortality and disability rate, decreasing very significantly the workload for Alert Operators and saving Health Care cost in total.

PUMAS Patenting major points:
1) To combine Mobile Medical, Police and Fire Emergency Alert into Wearable Personal Universal Mobile Alert System (PUMAS) wirelessly connected to local Medical, Police and Fire Emergency departments, local hospitals, private medical centers, doctors, local medical institutions through Regional Rapid Response Centers and provide customers with quickest possible Emergency intervention and help.

The Mobile Emergency Alert Devices combines GPS (Global Positioning Satellite) and cellular (GPS ground Cell Tower) technology, enabling Rapid Response monitoring Center to be notified of exact mobile client location and establish 2-way communication of client with local Rapid Response Centers, local hospitals, private medical centers, doctors, local medical institutions.

2) If PUMAS client is unable to push Alarm button, or is client sleeping, or in coma, or unconscious or for any other reason unable to speak and some of his Life Vital Signs current approaching Danger Red Zones, the Alarm operator has instantly on his display all client's private and medical information and immediately can take steps to provide help to client—without delay of precious time and without unnecessary precious time consuming "high workload".

To provide local Medical, Police and Fire Emergency teams through Regional Rapid Response Centers with client's life critical Medical Emergency information when Emergency Alarm signal is initiated by client to minimize response delay for quick intervention and help:

When Client pressing the PUMAS Alarm push button, the PUMAS mobile device will provide 2-way voice contact with local Rapid Response emergency monitoring center.

If client is silent and incapable for one minute to respond to Rapid Response Center after Alarm signal initiated, local Rapid Response Center automatically connects client location and his current Vital Signs information with local Medical, Police and Fire Emergency teams for quickest possible response and sends local Emergency teams to provide immediate help to client. The Emergency Team and Hospital Emergency Department have instantly clients current Vital Signs on screen.

If a personal client's Vital Signs are approaching the Vital Signs Red Danger zone and client does not initiate Alarm Signal push button, PUMAS automatically contacts local Rapid Response Center with client's current Vital Signs information to send Emergency Team to provide the help to client.

Accuracy of PUMAS Mobile GPS location is calculated by receiving direct Satellite GPS signals and does not depend on Cell Towers territorial distribution.

The new G5 technological standard provides clients with 10 feet mobile accuracy location in Emergency situation.

3) To provide continuous 7/24/365 monitoring, automatic intervention, feedback medical correction to PUMAS by medical office and help in case of Medical Vital Signs Red Line Life Danger and Geofencing crossing. PUMAS technology All PUMAS category devices have capacity for customized personal RF programming, providing auto intelligent feedback correction of client's medical condition as a reaction on client's medical Vital Signs, approaching Life Danger Red Lines borders by PUMAS continuous 24/7/365 monitoring of client's current Vital Signs, Police and Fire alarms.

The standard set of PUMAS technology is NOT meant for FDA regulated diagnostic applications of critical Vital Signs conditions.

Future PUMAS sets can be under FDA regulated diagnostic applications of critical Vital Signs conditions.

Additional Modification of Special PUMAS Wearable Wireless unit, Pendant/Medallion or Wrist device is to control Substance and Alcohol Abuse by Police and Fire departments and DMV.

Additional Modification of Personal Remote Wearable Wireless Geo Fencing unit, Pendant/Medallion or Wrist device is for the children Parental Control and Security/Protection.

Additional Modifications of Personal Remote Wearable Wireless units are possible for new bio sensitive sensors and medical conditions.

PUMAS Wearable Wireless bio sensitive patch can be placed on human skin at any place of human body.

All PUMAS devices have client's personal RF Radio Beacon transmitter to locate client's mobile location with GPS accuracy.

A Wearable Medical Alert electronic Tag/Emblem, a client's dangerous personal life chronic conditions to instantly alert Emergency Team and Doctors, incorporated into all PUMAS devices (Wrist, Basic units and Pendants/medallion/Wrist pushbutton), bearing a message that the wearer has an important medical condition that might require immediate attention. For emergency medical providers such as paramedics and emergency physicians, medical identification tags are particularly useful in situations where the wearer is unconscious, altered mental status, very young, or otherwise unable to provide critical medical information.

A type of medical identification alert is the USB and Wireless Wearable Medical Alert tag, essentially a USB flash drive with capacity to store a great deal of emergency information, including contacts and serious medical conditions. This Medical Alert information, in accordance with patient's personal health chronic conditions, will be mandatory installed by blue tooth or smart phone into all PUMAS devices and be accessible by any computer wirelessly or with a USB port at PUMAS basic device.

It should be protected from malware. The tag wirelessly incorporated into PUMAS should 100% belong to legal PUMAS client, excluding medical staff from risks to health and legal liability of medical personnel, if device is carried by an unconscious person may not be their own.

Additional new type of personal Medical Identification Alert is QR code based Medical Alert installed at all PUMAS devices. The QR code on the PUMAS links to a web service that contains the individual's emergency information. The information is accessed by any first Responder or Emergency personnel by scanning the QR code by using a smartphone or PUMAS devices. In addition to QR codes in all PUMAS devices included an embedded RFID chip that allows a first responder to simply tap their smart phone against the device. Since a web service is used to store the information in cloud, there is normally no limitation on how much information can be stored.

Examples of Medical Conditions tags to be installed in PUMAS and using typical conditions and prescriptions warranting. The wearing of such a tag includes but are not limited to:

Allergies, Adrenal Insufficiency Advance Medical Directives (Do Not Resuscitate, POLST, Lasting Power of Attorney, Living Will), Anaphylaxis allergies (food, drug, insect), Alzheimer's disease, Angioedema (hereditary), Anemia, Asthma, Asplenia, Autism, Cerebrovascular incident, Chemotherapy, Blood type (rare), Dementia, Diabetic (Type 1 and 2) Epilepsy, Hemodialysis, Hemophilia, Hypoglycemia, Hypopituitarism, Lamotrigine, Drug-induced Long-QT syndrome, Lymphedema risk, Use of a monoamine oxidase inhibitor (MAOI) drug, which can interact fatally with epinephrine, Memory disorders, Pacemaker or other implantable medical devices, Porphyria (acute), Seizure disorders, Situs inversus, Von Willebrand Disease, Plus over 100+ autoimmune diseases, including disorders, Anxiety, Parkinson's disease, Alzheimer's disease, Dementia, Multiple sclerosis, Epilepsy, Autism spectrum disorder, Depression, Anxiety Plus over 100+ autoimmune diseases, including disorders, Bipolar disorder, Hepatic encephalopathy, Neuropathic pain, and more.

PUMAS provides:

Electronic Health Records Recording and Archiving, Patent Personal Portals, Patent's Self-Monitoring, Early Disease Detection/Diagnostic, enables to Sense, Reason, Adapt and Correct client's Vital Signs information by clinicians, decreasing work load of Medical Alert operators and Emergency team, reduce the overall Health Care cost through 24/7/365 monitoring and automatic intervention into personal human life Vital Signs approaching danger Red Zones, decreasing (up to 92%) the mortality, morbidity and disability rate in case of Medical, Police and Fire Alert Emergencies.

Presently available WEARABLE WIRELESS biomedical customized Vital Signs sensors for PUMAS applications:

HEART: Heart Rhythm •Heart Rhythm Variability •Stress •Personalization •Heart Rate Training Zone •Heart Rate Recovery •Respiration Rate •More under development, ECG (electrocardiogram), PC (heart pacemaker) remote wireless adjustment by medical office to patient through PUMAS.

Heart Attack Detection

Arrythmia: Atrial FIB and Ventricular FIB

Blood Glucose monitoring for remote diabetes management/coma prevention.

Blood Oxygen

Blood Pressure (plastic smart bio sensitive band)

Wearable sensors guide Precision Remote Drug Dosing from medical office to patient through PUMAS.

Body Impedance (body poison remote wireless diagnostic)

Anemia

Dehydration

Chronic wound monitoring

*Cannabis* intoxication detection

Air contamination measurement

The changing of tumors size below the skin

Real-time, wearable wireless, continuous Auscultation to record and visualize modern auscultation (lung and heart diagnostic), to automate diagnoses of four types of disease in the lung, ranging from a crackle, to a wheeze, stridor and rhonchi, with 95% accuracy. The soft system is applicable for a sleep study to detect disordered breathing and to detect sleep apnea. Chronic obstructive pulmonary disease (COPD) and cardiovascular disease (CVD) are predominant factors of mortality worldwide.

Chronic obstructive pulmonary disease (COPD) and cardiovascular disease (CVD) are predominant factors of mortality worldwide. Accurate auscultation is helpful to diagnose disease at an early stage and evaluate the treatment response. Similarly, heart sounds also facilitate diagnosis and the identification of vascular heart diseases.

Wearable wireless infrared body Temperature

All/New future biomedical wearable wireless Vital Signs sensors, coming on the market and applicable for 24/7/365 Monitoring, Diagnostic and Intervention by clinicians through PUMAS.

PUMAS Standard Set

Personal Universal Mobile Alert Security System (PUMAS) has 3 Wearable Mobile devices: 1) Wearable Mobile Basic PUMAS device can work as standalone independent device to provide all PUMAS services or to be combined with standard Smart Phones into one Personal Universal Mobile Alert 24/7/365 System by Incorporating PUMAS into standard Smart Phone casing mechanically (by magnetic bar) with Bluetooth connectivity for recording and retransmitting of client's static and mobile personal data by Smart Phone.

No changes to smart phone itself.

Wearable Mobile Basic PUMAS device can work as independent standalone wearable mobile unit, having all PUMAS functions:

Direct Satellite Transponder for exact GPS calculations of client's mobile locations, client's static and mobile personal data, client's personalized current primary and secondary Vital Signs information, Exact Location Radio Beacon, Two-Way RF channel for client to communicate with Rapid Response Center, RF transponder for automatic intervention for continuous monitoring, correction and help in case of Medical Vital Signs Red Line Life Danger and Geofencing danger area crossing.

2) Wearable mobile waterproofed Wrist Bracelet with GPS exact location transponder, primary and secondary Vital Signs sensors with customized medical and/or fitness accuracy, Bluetooth and Wi-Fi connectivity, RF long distance transponder to Basic PUMAS device and to Regional Rapid Response Center.

User will set/customize in medical office his personal vital signs and the medical Life Danger Red Lines with medical level accuracy and set for Rapid Response Border Intervention when user is unable to push Emergency Alert button or incapable of speaking with Rapid Response Center.

PUMAS Emergency Alarm push button will send to Rapid Response Medical Center the Emergency Alarm with patient's static and mobile current Vital Signs information for local Medical, Police and Fire departments emergency teams.

Emergency teams will have patient's static and current Vital Signs information on the way to patient and do not need to spent time by taking Vital Signs at patient's location.

The Medical Emergency team will provide the patient's current Vital Signs information in advance to an appropriate hospital emergency department.

Medical Rapid Response Center will have patient's static personal information: patient's ID, address, prescribed medications, group of blood, allergy information, patient's doctor and hospital and relative's names and phone numbers and mobile current Vital Signs information with Life Danger Red Lines limits.

Police/Fire Rapid Response Center will have patient's personal ID, address and more information set by client himself, including medical information.

He can add his personal medical information—it could be helpful in case of an emergency.

The emergency team on the way to the patient will already have the personal Vital Signs of patient and send this information to hospital team specialized in emergency care of patient with such Vital Signs.

It will greatly reduce the delay time of medical intervention in hospital, providing medical help to patient during so-called (by doctors!) "golden" hour.

Doctors call the first hour to provide medical help in case of heart attack, stroke, diabetes emergencies as a "golden hour", greatly decreasing (up to 92%) the mortality and disability rate. In case of Police and Fire Alert emergencies it could be "golden minutes".

The PUMAS units should be powered independently by thin film lithium battery up to 72 operational hours per charge (or more).

3) PUMAS Wearable mobile Neck Pendant/Medallion or waterproofed Wrist pushbutton with its own mobile GPS location transmitter, continuous GPS monitoring and retransmitting of GPS exact location signal (G5 Standard, 10 feet accuracy) with transmission distance to PUMAS Basic at least distance of 200 feet:

PUMAS Personal Radio Beacon/Radio Medallion (transmission distance depending on power battery):

Configured as pendant, or medallion in pocket, or in purse, etc. to be a Personal Transmitter of RF Emergency Alert location in case of no response from client, when Emergency Alert signal initiated by Smart Phone or Wrist Bracelet Transponders.

Personal Beacon/Radio Pendant/Medallion and Wrist pushbutton has battery and GPS location chipset with transmitter of Emergency Location RF signal for at least 12 or more hours.

Wearable Waterproof Neck Pendant/Medallion or Wrist pushbutton Circuitry:

RF Power Supply

RF micro-Antenna

4) Wearable Wireless Waterproof PUMAS circuitry to receive and process biomedical Vital PUMAS biomedical patch/contact can be placed on the surface on human skin.

Pumas Setting:

Setting of mobile GPS tracking and geographic boundaries locations (geofencing) with Alarm notification (to be notified by Smart Phone if the geofencing perimeter is violated).

Bluetooth setting for static basic Vital Signs information recording.

Bluetooth setting for:

Personalized customized setting of personal Vital Signs

Sound Auto Reminder for taking medications.

Emergency Alarm Micro Push Button

Personal RF Radio Beacon transmitter of Emergency Exact Location and basic information set of static customized Vital Signal information.

RF Emergency Alarm 2-way WI-FI transponder with Smart Phone through local cell Towers activated by Alarm Emergency signal.

Laud Siren activated by Emergency push button.

Alarm Emergency Video activated by Emergency Alert signals.

PUMAS Vital Signs and Medical Alert information in Mobile Basic PUMAS System:

PUMAS Medical Alert set of personal Vital Signs will be customized by each client (through Bluetooth setting)

Specific Life Danger red line limits of Vital Signs will be customized for each client (depending on heart, lung, blood sugar etc. chronic health problems);

Critical Vital Signs readings, approaching specific Life Danger red lines limits, will start visible and sound Alarm signals on PUMAS Mobile Basic device, on PUMAS Smart Wrist bracelet display:

Rapid Response Center initiates the Rapid Response Help Intervention if client does not respond during 45 seconds after push button initiating of Medical or Police/Fire Emergency loud signal.

PUMAS Police/Fire Emergency Alarm channel will have client's personal, medical static and medical mobile information.

Patient's personal static information:

Patient's personal PUMAS ID, address, phone, email, medications, group of blood, patient's doctor, patient's hospital, patient's personal Vital Signs Red Line Life Danger limits information, names/phones to contact in case of Emergency, Patient's personal mobile information:

Patient's personal static information plus patient's mobile current Vital Signs information from Pumas Wrist Bracelet.

Basic Primary Personal Desirable Minimal Meagerable Vital Signs listing:

Heart Rhythm.

Heart Variable rate

Oxygen Saturation Rate/Pulse Oximetry

ECG (ELECTOGARDIOGRAM)

AFIB and VFIB

Blood Pressure (indirect estimation by Wrist Bracelet sensor information)

Blood Glucose/Sugar

Anemia

Life Danger Red Line limits of Vital Signs

Falling Alarm sensors

Secondary Desirable Meagerable Vital Signs Listing:

EEG (ELECTROENCEPHALOGRAPHY)

EMG (ELECTROMYOGRAPHY, electrical potential generated by muscle by neurologically activated)

Skin temperature and body impedance

Skin conductance (detect poison for unconscious patient)

Body impedance

Gait Speed

Environmental Danger signals:

Carbon Dioxide, Smoke, PM2.5 and PM10 (2.5 microns and 10 microns most dangerous pollutants), Volatile Organic Compounds/Allergenic (VOC)

Bio sensor on skin surface of mosquito-borne viruses for early very critical medical intervention Indiana Purdue University)

Leg diameter/swelling

Area Perimeter crossing lines (Geofencing)

Alarm Emergency Video activated by Emergency Alert signals.

Alarm Emergency Sound siren

PUMAS Measurable Vital Sings have potential for calculation of not measurable at present time Vital Signs Any new Wireless Wearable biomedical life Vital Signals on coming on market.

PUMAS Telemedicine applications:

PUMAs uses the telecommunication and information technology to provide remote Clinical Health care from a distance.

Telemedicine is to overcome distance barriers and to improve access to medical services that would often not be consistently available in distant rural communities. It saves lives in Critical Care, Medical, Police, Fire, Earthquake Emergency Situations and in Remote Advanced Diagnostic Methods supported by distributed client/server applications to local medical centers.

PUMAS have real time capacity for prediction for flu and infectious diseases.

PUMAS Tele-epidemiology applies satellite communication systems to investigate and support investigations of world infectious disease outbreak, including disease reemergence. In this application, PUMAS use the natural index and in-situ data (i.e. NDVI, Meteosat, Envisat) to assess health risk to human and animal populations. Space-based applications of tele-epidemiology extend to health surveillance and health emergency response in case of epidemic. Pumas technologies permit communications between patient and medical staff with both convenience and fidelity, as well as the transmission of medical, imaging and health informatics data from one site to another.

PUMAS Benefits and Applications

Telemedicine is beneficial to users in isolated communities and remote regions, who can receive care from doctors or specialists far away without the patient having to travel to visit them. Mobile Collaboration technology allow healthcare professionals in multiple locations to share information and discuss patient issues as if they were in the same place. Remote patient monitoring through Mobile Technology can reduce the need for outpatient visits and enable remote prescription verification and drug administration oversight, potentially significantly reducing the overall cost of medical care.

Almost two thirds of thoracic oncologists used telehealth for the first-time during pandemic.

PUMAS Telemedicine also facilitates medical education by allowing workers to observe experts in their fields and share best practices more easily. Telemedicine eliminates the possible transmission of infectious diseases or parasites between patients and medical staff.

PUMAS Market Base, Financial and Possible aspects:

Reductions in the cost of providing quality care to the chronically ill, estimated by the Center for Health Care Economics at the Milken Institute, exceeded $1.3 trillion just in USA alone per year in 2014 and is growing every year. In 2017 there were over 77 million senior citizens just in the USA and this number is growing every year.

Health Care costs will take over 18% of USA GDP in 2023, 2 times more than the Defense budget.

American Medical Association (AMA) estimated, that at least 50% of USA population now has at least one chronic debilitating disease and some have multiple such illnesses.

Add to these potential PUMAS users the workers of Construction, Agricultural, Transportation industries, Police and Fire Departments, private medical offices, Alarm Emergency demands in case of pandemic, fire and earthquake emergencies.

We are receiving an enthusiastic response from all potential PUMAS clients.

Before we introduced PUMAS on the USA market, already in some states the administrations, realizing Health Care saving, began to allocate state budget money to pay private clients for old simplified "push button" Medical Alert services.

PUMAS direct clients and business partners are Emergency Alert companies, who are between individual users and Rapid Response Centers.

Individual users are potential direct clients of Emergency Alert companies.

Individual users are potential indirect clients of PUMAS Business project.

PUMAS technology and wearable wireless service is the perfect instrument to generate consumable, from year to year, revenue for high quality PUMAS Medical Alert service and overall Health Care savings to state and country. FIG. 1 shows an example block diagram of an example with the PUMAS devices standard set with set of functional interconnections.

In some aspects, the simplified PUMAS block schematic information of FIG. 1 can be placed into multiple quadrats below, where each quadrat has a listing of specific logical functions to be performed. All quadrats are interconnected by logical functional lines and all functions in each quadrat and each logical functional line can include numerical ID: 1, 2, 3, etc.

In some aspects, under simplified PUMAS block schematic are placed descriptions of each function in each quadrat and each interconnectional logical functional line.

DESCRIPTION OF ASPECTS OF THE INVENTION

This disclosure is more clearly understood with aspects summarized in Appendix 1, which is incorporated herein by reference in its entirety as if set forth verbatim herein. It is understood that aspects of Appendix 1 are presented herein for purposes of illustration and should not be construed as limiting the scope of the disclosed technology in any way or excluding any alternative or additional embodiments.

The systems and methods of this disclosure are directed to systems and methods for personal universal, medical, police and fire security emergency alarm response coordinators. The systems and methods can including continuous monitoring (e.g., 24/7/365) user vital signs (e.g., user data stream) as a standalone independent system and/or wirelessly combined with any computing device(s) (e.g., a smart phone) thereby delivering users with prompt emergency response and coordinating first responder services (e.g., services by local Medical, Police and Fire local departments through Regional Rapid Response Centers in case of life critical and dangerous emergency situations).

In some aspects, the systems and methods of this disclosure can form part of personal area networks and work nationwide with Mobile Virtual Network Operators (MVNOs) as well as outside the US with cellular network providers.

In some aspects, users and beneficiaries of the systems and methods of this disclosure can be individuals as well as emergency alert companies, who are between individual users and rapid response centers. In some aspects, users and beneficiaries of the systems and methods of this disclosure can be direct clients of Emergency Alert companies and/or indirect clients of the system itself.

Furthermore, as a result of most privacy laws, personal and medical information is protected by law and unlawful dissemination can arise to both civil and criminal exposure. For example, medical contracts can require a user's permission to limits where and how to use personal user's information. In response, most emergency alert companies have developed proprietary two-way encrypted, enciphered communication channels between users and emergency alert operators. As such, emergency alert units, bracelets and medallion devices are similarly designed with this encryption between user and operator, one point to one point. This 2-way channel is also protected from smart phone channels and this is the platform of emergency alert companies, imposed on all emergency alert devices. Therefore, in view of the numerous different and conflicting encryption approaches, any universal system and method cannot work with all emergency alert companies.

Figure 2A:
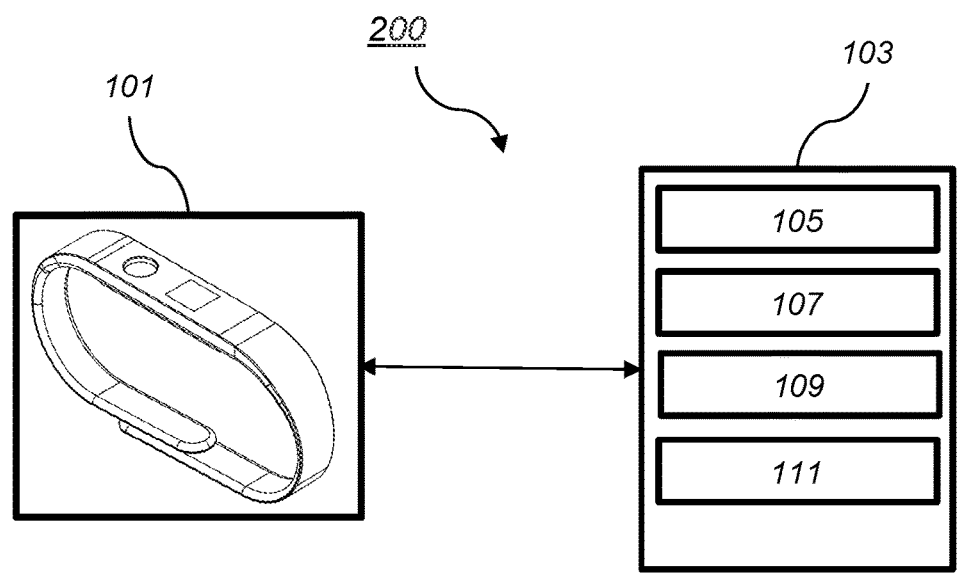
FIG. 2A illustrates an example block diagram of an example monitoring and alert system, according to an example embodiment.

Referring to FIG. 2A, an example block diagram is shown of personal universal monitoring and alert system 100.

System 100 can receive and analyze information (e.g., user data stream) from one or more wearable monitor devices 101 configured to be donned by a user to continuously monitor, store, and transmit information related to the user. Device 101 can be wireless enabled and be formed from any suitable material, including but not limited to plastic, gold, silver, any metallic alloy or any combination of suitable materials. Device 101 can include a transceiver attached to or embedded in its band. In one embodiment, the transceiver is connected to the band of device 101 and uses the band as an antenna for receiving, transmitting, and/or receiving inductive energy. In some aspects, the band of device 101 can be in the shape of a bracelet and include a smart wrist display.

In some aspects, the band of device 101 can included personal customized biomedical Vital Signs sensors circuitry, transmitter from Wrist Unit to Basic Unit the current Vital Signs from Vital Signs sensors, GPS transponder/Mobile location beacon, client's personal customized Medical Identification Alert QR code tag/emblem (chronic/genetic), customer personal customized Medical/Allergy Conditions tag, client's personal static information (name, address, phone, physician, hospital, etc.), client's personal customized Danger Zone, RF transponder for automatic intervention through Basic Unit for correction and help by medical office, when client's vital signs are approaching the life Danger Zone.

Regarding connectivity, device 101 can include RF input to set all customized Vital Signs parameters and adjust embedded devices from medical office (by phone or/computer), an RF charging power supply with power charging indicator, and Emergency Alert pushbutton.

In some aspects, the bracelet example of device 101 can be a wearable mobile waterproofed wrist bracelet with one or more GPS location transponders as well as primary and secondary vital signs sensors with customized medical and/or fitness accuracy, Bluetooth and Wi-Fi connectivity, RF long distance transponder (e.g., with a transmission distance of at least a distance of 1000 feet) and configured to communicate with third party first responders (e.g., regional rapid response center).

In some aspects, device 101 can include a personal current biomedical Vital Signs receiver working in silent mode, and transmitting Medical Alert information to local Medical Alert operators when client's Vital Signs are approaching Danger Zones and cloud storage for recording Two-Way RF laud channel for client to communicate with local Rapid Response Center operators. Device 101 can include GPS transponder/Mobile location beacon as well as Client's personal customized Medical Identification Alert QR code.

In some aspects, device 101 can include Client's personal customized Medical Identification Alert QR code tag/emblem (chronic/genetic), Customer personal customized Medical/Allergy Conditions tag, Client's personal static information (name, address, phone, physician, hospital, etc.), Client's personal customized Danger Zones, Connectivity circuitry to communicate with local Medical Alert operator, Connectivity circuitry to communicate with Wrist unit to adjust embedded devices, Electrical power supply cradle to charge Basic unit and RF power supply to charge Wrist unit with power charging indicator, and/or an Emergency Alert pushbutton.

In some aspects, cloud information storage can include Electronic Health Records Recording and Archiving, Patent Personal Portal, Patent's Self-Monitoring, Early Disease Detection/Diagnostic, enables to Sense, Reason, Adapt and Correct client's Vital Signs information by clinicians, decreasing work load of Medical Alert operators and Emergency team, reduce the overall Health Care cost through 24/7/365 monitoring and automatic intervention into personal human life Vital Signs approaching danger zones.

In some aspects, device 101 can be a customized waterproof pendent/medallion/wrist pushbutton unit. The device 101 can include client's Personal Radio Beacon/Radio battery and GPS location chipset for transmitter Emergency Location to PUMAS Basic unit or smart phone, setting of mobile GPS tracking and geographic boundaries locations (Geofencing) with Alarm notification (to be notified by PUMAS Basic unit or by smart phone if the geofencing perimeter is violated) when child is crossing the Geofencing bounders, Rf circuitry to except the setting from smart phone the customized Geofencing bounders, Lithium battery, replaced after 3 Years of operation, rf micro antenna, and an emergency Alarm micro push button.

In another embodiment, the transceiver's antenna of device 101 is included on a chip or board of the transceiver. Device 101 can include a memory which stores and/or otherwise records user information as well as sensed information in real time (e.g., via sensors onboard device 101 such as heart rate sensors, temperature sensor, etc.). In some aspects, sensors of device 101 can be configured to sense heart rhythm, heart rhythm variability, stress, heart rate training zone(s), heart rate recovery, respiration rate, heart attack detection, body impedance, chronic wound monitoring, atrial fibrillation, ventricular fibrillation, ambient air contamination, tumor size, disordered breathing (e.g., to detect sleep apnea), and auscultation.

With respect to cardiac analytics, the system 100 can include enabled wireless transmission of ECG from a moving ICU van or a user's home to the central station in an ICU. System 100 can connect with a central control unit at the ICU (e.g., via network 108 and/or external resources 116) to facilitate interpretation of conditions such as arrhythmia. With respect to auscultation, logic applied by system 100, including device 101, can be configured to automate prediction and/or diagnosis of multiple types of disease in the lung, ranging from a crackle, to a wheeze, stridor and rhonchi. Chronic obstructive pulmonary disease (COPD) and cardiovascular disease (CVD) are predominant factors of mortality worldwide. In this respect, accurate auscultation detection by system 100 is particularly advantageous to diagnose disease at an early stage and evaluate the treatment response. Device 101 can also be configured to wirelessly measure and adjust implanted medical devices of a user (e.g., a pacemaker) as well as manage precision remote drug dosing. Measurements sensed by sensors of device 101 can also be represented in one or more visual displays.

Sensors of device 101 can also include one or more cameras (e.g., body camera), sensors to measure ambient temperature, moisture, accelerometers to detect acceleration such as a rapid fall of the user, telemetry data, location data, etc. Sensors of device 101 can also include infrared sensors and can include wireless transceivers so as to transmit user data. Based on the detected user information from the one or more sensors, the device 101 may be configured to generate a continuous user data stream.

In some embodiments, there may be more than one device 101. For example, the user may have a wrist band monitor and a neck pendant monitor that both generate user data streams. While device 101 is shown in FIG. 2A as a wearable band, it is understood that device 101 could be any number of other devices types (e.g., a wearable ring, a wearable patch, a wearable garment, etc.). For example, the device

101 may be a neck pendant, or a medallion, among other forms, each including an RF micro-antenna and RF power supply.

In some aspects, the sensors of device 101 can include one or more modes, such as active mode for users detected as having an active life style where sensors are less sensitive to motion. Examples active mode scenarios include users camping, hiking, boating, and the like. The sensors of device 101 can include a monitoring mode where the user is detected as having a passive life style where sensors are more sensitive to motion.

In some aspects, the device 101 can detect information that includes location, pulse, medication levels in the patient (e.g., insulin levels), information related to user blood (e.g., clotting factor level), information related to user blood pressure, body temperature, and respiratory rate. System 100 can also include one or more user computing devices 103, such as a mobile device. Device 103 may include a memory 105, a processor 107, an application 109, and a network access device 111. The different components, such as device 101 and device 103 may interconnect with each other through a network (e.g., network 108 of FIG. 2B).

The device 101 may include a message that the wearer has an important medical condition that might require immediate attention. For emergency medical providers, such as paramedics and emergency physicians, can utilize medical identification tags that include such messages are particularly useful in situations where the wearer is unconscious, altered mental status, very young, or otherwise unable to provide critical medical information. In some aspects, the tag is made of sterling silver. In some aspects, the device 101 can include detachable memory in the form of a removable USB flash drive that includes stored static user information, such as emergency information, including contacts and medical conditions. In some aspects, the device 101 can also include a secure first responder channel configured to communicate with one or more first responders in the event the user is outside a user-specific safe zone and/or within a danger zone, where the secure first responder channel includes stored static user information, such as emergency information, including contacts and medical conditions. The term "static user information" can include a patient's user identification, address, phone, email, medications, blood type, allergy information, patient's doctor, patient's hospital, patient's personal zone information (e.g., safe zone, intermediate zone, danger zone, etc.), emergency contacts, etc.

In some aspects, the device 101 can be configured to produce a QR code based medical alert on a sticker as well as a user interface display. The QR code on device 101 can to a web service that contains user related information, such as emergency information as well as user related analytics, vital sign information, medical conditions, and/or the like. The information can be accessed by one or more first responders (e.g., emergency) by scanning the QR code. In some aspects, one or more embedded RFID chips of the device 101 can be included to allow a first-responder to simply tap their phone against the device 101. The term "first responder" means one or more persons and/or systems with specialized training among the first to arrive and provide assistance or incident resolution at the scene of an emergency or event requiring response, such as an a health scare (e.g., an event defined by a user being in a danger zone and/or not in a safe zone) accident, disaster, medical emergency, structure fire, crime, terrorist attack, and/or the like. A "first responder" can include law enforcement, fire fighters, paramedics, other responding care providers to emergencies and/or natural disasters (e.g., such as an earthquake, hurricane, tornado, or other such extreme event) as well as close family members and neighbors.

The device 103 may have an application 109 loaded on the device 103. The application 109 may control, manage, communicate and/or otherwise interact with device 101. The application 109 may be stored in the memory 105. The memory 105 may store instructions to execute on the processor and may include one or more of a RAM or other volatile or non-volatile memory. The memory 105 may be a non-transitory memory or a data storage device, such as a hard disk drive, a solid-state disk drive, a hybrid disk drive, or other appropriate data storage, and may further store machine-readable instructions, which may be loaded and executed by the processor 107. In some aspects, device 103 can include a 2-way channel can with an RF emergency alarm 2-way Wi-Fi transponder with Smart Phone through local cell Towers activated depending on the user state (e.g., safe zone, danger zone, etc.).

The processor 107 may be a single processor or multiple processors. The processor 107 may receive data from one or more components and control the operations of the one or more components based on the received or determined data. For example, the processor 107 may run the application 109. In some implementations, the processor 107 may be multiple processors, such as a dual processor.

The application 109 may include interface and/or interact with a user interface. The user interface may include any device capable of receiving user input, such as a button, a dial, a microphone, a graphical user interface or a touch screen, and any device capable of output, e.g., a display, a speaker, or a refreshable braille display. The user interface allows a user to communicate with the application 109. The user interface may display notifications and/or confirmations.

The device 103 may use the network access device 111 to establish a connection with the device 101. The network access device 111 may include a communication port or channel, such as one or more of a Wi-Fi unit, a Bluetooth® unit, a radio frequency identification (RFID) tag or reader, or a cellular network unit for accessing a cellular network (e.g., 3G or 4G). The network access device 111 may transmit data to and receive data from devices and systems not directly connected to the device 103. For example, the application 109 may communicate with the device 101 through a network (e.g., network 108 of FIG. 2B).

The device 103 may include a radio frequency (RF) beacon to allow the user to be geographically located. In some embodiments, the device 103 may include a GPS (Global Position System) transmitter and/or use GSM (Global System for Mobile Communications) to allow the user to be geographically located. The device 101 may similarly include a radio frequency (RF) beacon to allow the user to be geographically located. In some embodiments, the device 101 may include a GPS (Global Position System) transmitter and/or use GSM (Global System for Mobile Communications) to allow the user to be geographically located. In some embodiments the device 101 and/or the device 103 may incorporate G4 and/or G5 technology (e.g., with approximately 300 centimeter location accuracy).

The device 101 may have a speaker and/or light to provide a visual or audio reminder for the user take their prescribed medication. In some embodiments, the device 101 may be configured to allow two way communications between the user and a first responder (e.g., a regional rapid response center). The regional rapid response center may dispatch to a physician, a surgeon, a medical specialist, a nurse, a hospital, a treatment facility, an emergency operator, a police department, or fire department among others. In other embodiments, the application 109 may remind the user take prescribed medication.

The device 101 may have a button configured to initiate communication with the regional rapid response center when the button is actuated. In some embodiments, the communication may be in the form of an alert. In other embodiments, the communication may be in the form of two-way communication.

Figure 2B:
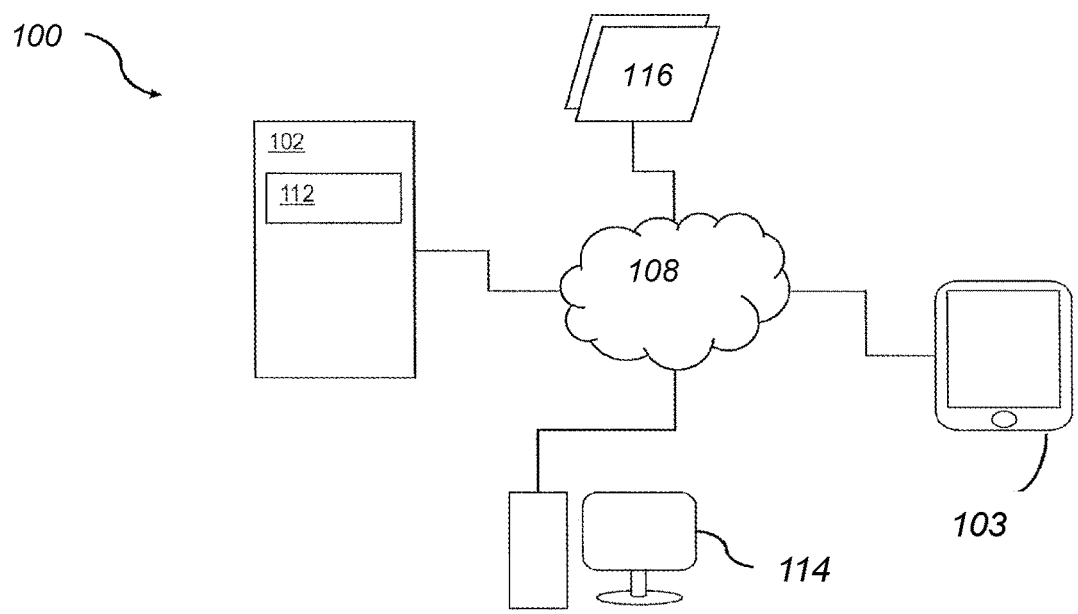
FIG. 2B illustrates a system having one or more features consistent with the present description.

FIG. 2B illustrates another example system 100 including a server 102 that has a memory 104. The memory 104 can include one or more databases including user related information. For example, user related information can include data streams related to the user as well as unrelated to the user from one or more physician servers, hospital servers, first responder servers (e.g., police, fire, and other emergency personnel), and the like, that may create or otherwise obtain or include user information. Any of the one or more servers in contact with or included with server 102 may also obtain any combination of user-specific information, such as age, location, pulse, medication levels in the patient (e.g., insulin levels), information related to user blood (e.g., clotting factor level), information related to user blood pressure, body temperature, respiratory rate, related medical history, medication history, family history, etc.

Memory 104 may include electronic storage media that electronically stores information. The electronic storage media may include one or both of system storage that is provided integrally (i.e., substantially non-removable) with a computing device, such as device 103 that is removably connectable to server 102 via, for example, a port (e.g., a USB port, a firewire port, etc.) or a drive (e.g., a disk drive, etc.). Memory 104 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Memory 104 may include one or more virtual storage resources (e.g., cloud storage, a virtual private network, and/or other virtual storage resources). Memory 104 may store software algorithms, information received from one or more computing devices, such as server 102, client computing devices, such as mobile computing device 103, information that enables the one or more computing device to function, or the like.

The server 102 can include a processor 112 configured to provide information processing capabilities to a computing device having one or more features consistent with the current subject matter. Device 103 in the depicted example can be a smart phone, tablet, desktop computer, and the like. Processor 112 may include one or more of a digital processor, an analog processor, a digital circuit designed to process information, an analog circuit designed to process information, a state machine, and/or other mechanisms for electronically processing information. Although processor 112 is shown in FIG. 2B as a single entity, this is for illustrative purposes only. In some implementations, processor 112 may include a plurality of processing units. These processing units may be physically located within the same device, or processor 112 may represent processing functionality of a plurality of devices operating in coordination. For example, some of the functions of processor 112 may be performed by device 103, server 102, one or more other computing devices 114 and the like. The processor 112 may be configured to execute machine-readable instructions, which, when executed by the processor 112 may cause the processor 112 to perform one or more of the functions described in the present description. The functions described herein may be executed by software; hardware; firmware; some combination of software, hardware, and/or firmware; and/or other mechanisms for configuring processing capabilities on processor 112.

Any of the one or more servers in contact with or included with server 102 may transmit user data over network 108. Network 108 can be a Bluetooth Low Energy (BLE) network, a local area network (LAN), a wide area network (WAN), a cellular network, the Internet, or combination thereof, connects the device 103 to the device 101 and/or a server. The server may be a trusted application management (TAM) server, for example.

Server 102 may further include one or more machine learning tool(s) or capabilities. For example, the processor 112 may include a machine learning tool for detecting whether a user is presently or predict to be in a safe zone, an intermediate zone, and/or a danger zone of the user, according to one embodiment. Alternatively or in addition, the present disclosure (or portions of the system and methods of the present disclosure) may be performed on a local processing device (e.g., device 103). Each zone can be associated with a particular vital sign range of the user as well as be based on user-specific historical data. The vital sign range of the safe zone can in some aspects depend on heart rate, blood pressure, oxygen saturation, blood sugar levels, as well other factors related to chronic health problems. In some aspects, boundaries of the respective zones can be customized or otherwise revised by the end-user and/or physician remotely through one or more connected computing devices (e.g., device 103).

Vital signs considered in classifying data from the user data stream, determining user specific zones, determining and/or predicting user states related therewith, can include heart rate, heart variable rate, oxygen saturation rate, pulse oximetry, electrocardiogram (ECG), breathing rate, blood pressure, heart arrhythmia, blood glucose, physiological boundary limits, physically falling, electroencephalography (EEG), electromyography (EMG), skin temperature, blood alcohol, other substance levels in blood, body impedance, skin conductance, loss of blood, loss of plasma, loss of blood sodium, changes in the diameter of the individuals extremities, or gait speed. Other user data sensed, stored, and conditions considered by system 100 and its components can include Adrenal insufficiency, Advance Medical Directives, Anaphylaxis allergies, Alzheimer's disease, Angioedema, Anemia, Asthma, Asplenia, Autism, Cerebrovascular incident, Chemotherapy, Blood type (rare), Dementia, Diabetic (Type 1 and 2), Epilepsy, Hemodialysis, Hemophilia, Hypoglycemia, Hypopituitarism, Lamotrigine, Drug-induced Long-QT syndrome, Lymphedema risk, Use of a monoamine oxidase inhibitor (MAOI) drug, which can interact fatally with epinephrine, Memory disorders, Pacemaker or other implantable medical devices, Porphyria (acute), Seizure disorders, Situs inversus, Von Willebrand Disease, and the like.

In some variations, external resources 116 can provide additional information or add-on information. External resources 116 can include one or more databases in communication with one or more rapid response centers for controlling operations of corresponding first responder(s) and/or other third party systems (e.g., government offices such as the criminal justice system (e.g., to communicate user information detected by system 100 with respect to the user and related case(s) such as parole), Department of Motor Vehicles (e.g., to communicate information detected by system 100 regarding aspects relevant to user driver information such as substance levels), public health departments, etc. As used herein, the term "in communication" means direct and/or indirect communication through one or more intermediary components and does not require direct physical (e.g., wired and/or wireless) communication, including selective communication and/or one-time events. Rapid response centers associated with external resources 116 can be configured to coordinate alarm response operations (e.g., communicate user vital sign information, required medications, current user medical states, and coordinate with appropriate first responder while supply said first responder with necessary user information to provide quicker attention to the user).

In one embodiment, external resources 116 can include a location database including real-time continuous location data of first responder personnel (e.g., a firefighter, an ambulance driver, a law enforcement officer, etc.). For example, the application executed on device 103 and/or supported by the server 102 can be configured to obtain user data from one or more third party servers in order to determine and/or predict whether the user is or will be imminently in the safe zone, the intermediate zone, and/or the danger zone. In some aspects, once the system determines or otherwise identifies critical vital signs readings approaching boundaries of the safe zone and/or entering the danger zone, one or more alarms can be transmitted and presented locally with audio and/or visual feedback (e.g., housing of device 101 can light up red or emit an alarm sound). In some aspects, LED light indicators of the housing of device 10 can include colorized emergency indicators (e.g., flash and/or light up blue for law enforcement, orange for fire, red for hospital, flash to distinguish for urgency, etc.). In some aspects, the housing of device 101 can be detachable so as to interchange aspects thereof (e.g., interchange the back cover, the front cover, etc.) to render the housing more durable and/or desirable to the user.

In some aspects, for every user, there are medically officially established Reference Range (Normal Limits) for each human Vital Sign. In some aspects, when Vital Sign is in limits of its Reference Range, then the system can define this as the safe zone. When Vital Sign is not in Reference Range, the system can define this as the Danger Zone. In some aspects, for each client the customized Reference Range for each Vital Sign can be established in medical office wirelessly by smart phone or computer, in a few minutes.

When any of customized Vital Sign crossing its Red Line, the system triggers the Alarm Signal and transmits all client's static and current Vital Signs. All local Alert operators and Medical Alert teams instantly will see on display all client's static information and all his current Vital Signs, including Vital Sign that is crossing its danger Red Line, it is the life Danger Red Zone.

When all client's current Vital Signs are in Reference Range, the system is working in silent mode. When any of customized Vital Signs crossed the Reference Range limits, it is the life Danger Zone and the system can start to transmit Medical Alarm signal and all client's static information and current Vital Signs. For example, Reference Range for human heart rhythm is between 55 and 110 beats per minute. If heart rhythm is below or above Reference Range, the heart rhythm is in Danger Zone.

In some aspects, in a focused infrared beam continuous radiation method, breathing in high levels of Nitrogen Dioxide increases the risk of respiratory problems. Coughing and difficulty breathing are common and more serious health issues such as respiratory infections can occur with longer exposure.

In some aspects, fine particulate matter is inhalable pollutant particles with a diameter less than 2.5 micrometers that can enter the lungs and bloodstream, resulting in serious health issues. The most severe impacts are on the lungs and heart. Exposure can result in coughing or difficulty breathing, aggravated asthma, and the development of chronic respiratory disease.

In some aspects, particulate Matter is inhalable pollutant particles with a diameter less than 10 micrometers. Particles that are larger than 2.5 micrometers can be deposited in airways, resulting in health issues. Exposure can result in eye and throat irritation, coughing or difficulty breathing, and aggravated asthma. More frequent and excessive exposure can result in more serious health effects.

In some aspects, round-level Ozone (O 3) can aggravate existing respiratory diseases and also lead to throat irritation, headaches, and chest pain. Exposure to Sulfur Dioxide can lead to throat and eye irritation and aggravate asthma as well as chronic bronchitis.

In some aspects, Carbon Monoxide is a colorless and odorless gas and when inhaled at high levels can cause headache, nausea, dizziness, and vomiting. Repeated long-term exposure can lead to heart disease.

In some aspects, in a focused infrared beam continuous radiation method, breathing in high levels of Nitrogen Dioxide increases the risk of respiratory problems. Coughing and difficulty breathing are common and more serious health issues such as respiratory infections can occur with longer exposure.

In some aspects, fine particulate matter is inhalable pollutant particles with a diameter less than 2.5 micrometers that can enter the lungs and bloodstream, resulting in serious health issues. The most severe impacts are on the lungs and heart. Exposure can result in coughing or difficulty breathing, aggravated asthma, and the development of chronic respiratory disease.

In some aspects, particulate Matter is inhalable pollutant particles with a diameter less than 10 micrometers. Particles that are larger than 2.5 micrometers can be deposited in airways, resulting in health issues. Exposure can result in eye and throat irritation, coughing or difficulty breathing, and aggravated asthma. More frequent and excessive exposure can result in more serious health effects.

In some aspects, round-level Ozone ($O_3$) can aggravate existing respiratory diseases and also lead to throat irritation, headaches, and chest pain. Exposure to Sulfur Dioxide can lead to throat and eye irritation and aggravate asthma as well as chronic bronchitis.

In some aspects, Carbon Monoxide is a colorless and odorless gas and when inhaled at high levels can cause headache, nausea, dizziness, and vomiting. Repeated long-term exposure can lead to heart disease.

In some aspects, human heart rhythm changing all time and depends on physical activity, danger, mental stress, etc. It can be changed in few seconds, specific for every human. It controls by brain electric signals and hormones. As long as heart rhythm is in normal limits of established Reference Range, it is normal.

In some aspects, system 100 can include one or more external plugins to return queries from and coordinate with third party ride share services, including Uber, Lyft, and the like. In some aspects, system 100 can include a third party interface layer configured to receive information from ride share application programming interfaces (APIs) of any current or to be developed ride share service so as to allow for a wide range of ride coordination techniques to be integrated and accessed based on the user data stream and resultant determined need of the user. In one example, if a user is having symptoms and not feeling good yet device 101 has not detected that the user is outside the safe zone or in the danger zone, the user can manually cause an alert communication to be transmitted to the physician's office and request a transportation to and from the physician's office. In some aspects, the physician's office can continuously receive information from the user data stream, including all detected vital sign information, related analytics and predictions by system 100 thereby minimizing time in the waiting room and expediting treatment to the user.

In some aspects, system 100 can include one or more external plugins to return queries from and coordinate with third party telemedicine service providers. The term "telemedicine" as used herein can be broken into categories such as store-and-forward, remote patient monitoring, and/or real-time interactive services. In some aspects, the system 100 can include a telehealth improvement module that analyzes telehealth performance to determine effectiveness of rapid response actions in response to a user health zone alert and to improve the system through targeted interventions, including remote monitoring of post-operational period, remote therapy instructions and help. In some aspects, the telehealth improvement module can be configured to identify services for patients in need of special medical care, lifestyle, and fitness coaching for wellness or health risk reduction. In some aspects, the telehealth improvement module works closely with the administrative component, clinicians, and quality improvement experts to evaluate measures such as outcomes measures, process measures, and balancing measures. In some aspects, balancing measures implemented can be configured to evaluate any unintended consequences of the rapid response. The telehealth improvement module can also be configured to identify barriers to activating the MET include the primary team's overconfidence in their ability to stabilize the patient, poor communication, hierarchal problems, and hospital culture.

Telemedicine examples when used with system 100 can utilized for trauma triage whereby trauma specialists can remotely interact with personnel on the scene of a mass casualty or disaster situation, via the internet using devices of system 100 (E.g., devices 101, 103), to determine the severity of injuries. Trauma specialists and related systems can clinically assess and determine whether injured users must be evacuated for necessary care. Remote trauma specialists of this particular example can provide the same quality of clinical assessment and plan of care as a trauma specialist located physically with the patient.

In the ICU specifically, system 100 is particularly advantageous as it reduces the spread of infections. In a hospital setting, ICU rounds are usually conducted at hospitals across the country by a team of approximately ten or more people to include attending physicians, fellows, residents and other clinicians. This group usually moves from bed to bed in a unit discussing each patient. This aids in the transition of care for patients from the night shift to the morning shift, but also serves as an educational experience for new residents to the team. A new approach features the team conducting rounds from a conference room using a video-conferencing system. The trauma attending, residents, fellows, nurses, nurse practitioners, and pharmacists are able to watch a live video stream from the patient's bedside. The ICU team can see the vital signs on the monitor, view the settings on the respiratory ventilator, and/or view the patient's wounds. Video-conferencing allows the remote viewers two-way communication with clinicians at the bedside.

In some aspects, the telemedicine examples of system 100 can include "telerehabilitation", which is understood herein as including the remote administration and delivery of rehabilitation services (e.g., over telecommunication networks and the Internet). Telerehabilitation" as used herein can include clinical assessment as well as clinical therapy.

In some aspects, the telemedicine examples of system 100 can include "teleradiology", which is understood as including the remote administration and delivery of radiology services (e.g., transmission and analytics of radiographic images such as x-rays, CT, MR, PET/CT, SPECT/CT, MG, US, etc.

"Store-and-forward" as used in the aspects of the systems and methods of this disclosure can be understood as acquiring medical data (e.g., medical images, bio signals, blood test results etc.) and then transmitting this data to medical specialist at a convenient time for assessment offline. Store-and-forward does not require the presence of both parties at the same time. Dermatology (e.g., tele dermatology), radiology, and pathology are specialties contemplated for use with telemedicine examples of this disclosure. The 'store-and-forward' process requires the clinician to rely on a history report and audio/video information in lieu of a physical examination.

"Remote monitoring" as used in the aspects of the systems and methods of this disclosure can be understood as self-monitoring or testing, enables medical professionals to monitor a patient remotely using various technological devices. This method is primarily used for managing chronic diseases or specific conditions, such as heart disease, diabetes mellitus, or asthma. Such "remote monitoring" services can provide comparable health outcomes to traditional in-person patient encounters, supply greater satisfaction to patients, and may be cost-effective. Examples include home-based nocturnal dialysis and improved joint management.

In some aspects, the telemedicine examples of system 100 can include "telenursing", which is understood as including the use of telecommunications and information technology in order to provide nursing services in health care whenever a distance exists between patient and nurse(s), for uses such as telediagnosis, teleconsultation, telemonitoring, etc.

In some aspects, the telemedicine examples of system 100 can include "telepharmacy," which is understood as including the delivery of pharmaceutical care via telecommunications to patients in locations where they may not have direct contact with a pharmacist. Telepharmacy services contemplated for use with system 100 can include videoconferencing with pharmacists as well as remote drug therapy monitoring, remote patient counseling, remote prior authorization and refill authorization for prescription drugs, and remote monitoring of formulary compliance with the aid of teleconferencing or videoconferencing. Remote dispensing of medications by automated packaging and labeling systems can also be include. Telepharmacy services can be connected in system 100 and delivered at retail pharmacy sites or through hospitals, nursing homes, or other medical care facilities.

In one example, similar to ride share coordination, based on user data detected and analyzed by system 100 (including by device 101), one or more alert communications can be transmitted to the third party telemedicine service providers and so that the respective third party telemedicine service provider can consider the feedback and take and/or otherwise coordinate appropriate action.

In some aspects, system 100 can include real time capacity for prediction for flu and infectious diseases. For example, system 100 can be used with tele-epidemiology applications whereby external resources 116 can include databases of satellite communication systems, such as data related to infectious disease outbreak, including disease reemergence. In some aspects, if the real time health monitoring of a user indicates an infection of a potentially harmful pathogen, additional safety precautions may be taken by first responders associated with system 100 (e.g., emergency personnel and other medical staff) to ensure that the infection does not spread beyond the user. Moreover, any individuals infected with a pathogen may be located and treated in the early stages of the outbreak to prevent widespread infection among the rest of the population. In some aspects, system 100 can include one or more predictor modules (e.g., located locally in memory of device 101 or remotely connected thereto such as with external resource 116) to classify, based on one or more data feeds (e.g., user data stream, infectious disease outbreak data feeds, disease reemergence feeds, etc.) event type, event location, disease type, disease location, disease response, as well as user response based on analyzed user data, determined response related to continuously monitored user vital sign, environmental data, and/or infectious disease data, and then determine, based on classifying whether the user is in or predicted to be in a safe zone, an intermediate zone, a danger zone, as well as related infectious disease analytics, one or more user alert and/or infectious disease response actions.

In some aspects, data feeds associated with infectious disease can include natural index and in-situ data (e.g., data feeds from NDVI, Meteosat, Envisat, etc.) to assess health risk to human and animal populations. Space-based applications of tele-epidemiology extend to health surveillance and health emergency response in case of epidemic. Computing methods to implement this logic and coordinate associated responses can include, but are not limited to, statistical analysis, autonomous or machine learning, and AI. AI may include, but is not limited to, deep learning, neural networks, classifications, clustering, and regression algorithms. By using such computing methods, alert identification and analytics related to event type identification and/or appropriate response actions is substantially improved as is reliability and efficiency.

In some aspects, a computing system operating one or more of the foregoing computing methods can include a trained machine learning algorithm that takes, as input, any of the herein disclosed data feeds as well as historical databases, and determines whether one or more salient events or trends are occurring and exceed a predetermined threshold according to user data and/or infectious disease assessment logic. If exceeded, a response by system 100 can be coordinated. Many methods may be used to learn which aspects of the foregoing data feeds are salient to the extent one or more alerts are merited, including but not limited to: (1) weak supervision: training a machine learning system (e.g., multi-layer perceptron (MLP), convolutional neural network (CNN), graph neural network, support vector machine (SVM), random forest, etc.) using multiple instance learning (MIL) using weak labeling of the digital image or a collection of images; the label may correspond to the presence or absence of a salient areas; (2) bounding box or polygon-based supervision: training a machine learning system (e.g., region-based CNN (R-CNN), Faster R-CNN, Selective Search) using bounding boxes or polygons that specify the sub-regions of the digital image that are salient for the detection of the presence or absence of one or more markers related to a potential alert (3) pixel-level labeling (e.g., a semantic or instance segmentation): training a machine learning system (e.g., Mask R-CNN, U-Net, Fully Convolutional Neural Network); and/or (4) using a corresponding, but different digital image that identifies one or more alerts and/or response actions.

In some aspects, the device 101 is configurable with device 103 to facilitate customization of related third party apps and vital sign boundaries for user zone classification, user zone prediction, and/or transmission of related communication(s) with respect to one or more other apps of device 103. With this integration with ride share platforms, the system 100 will also be capable of coordinating ride services or even rentals in when the user's vehicle is unavailable, when communicating with insurance companies regarding their vehicle, as well as reserving customers a vehicle in case they are late to school, work and or any other event.

Figure 3:
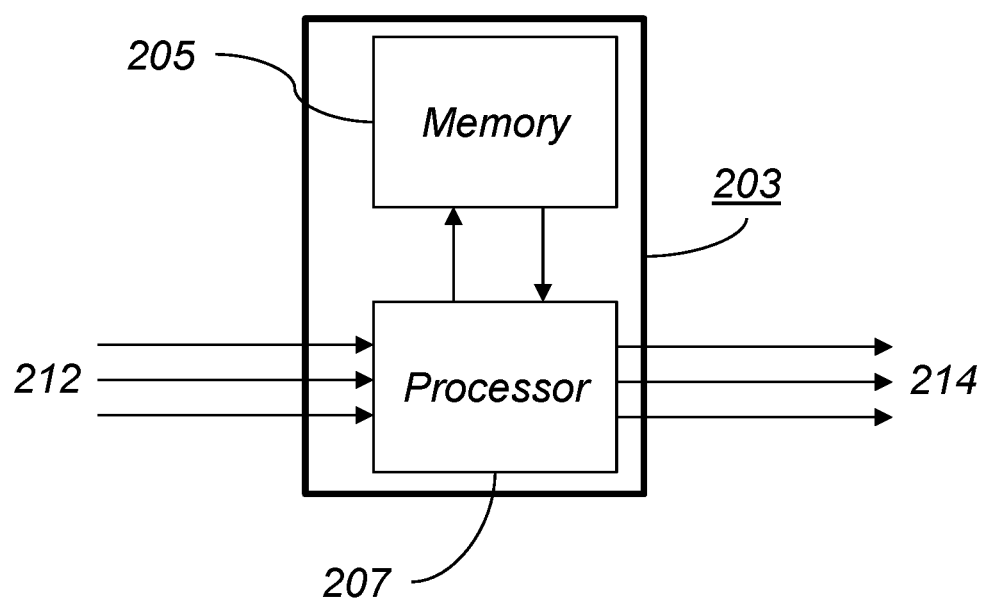
FIG. 3 shows an example mobile device for user monitoring, according to an example embodiment.

FIG. 3 shows an example computing 203 contemplated for use with system 100, which is similar to previously discussed device 103 and like parts are numbered similarly. The mobile device 203 includes a memory 205 and a processor 207. The memory 205 may store an application. The memory 205 may store instructions to execute on the processor and may include one or more of a RAM or other volatile or non-volatile memory. The memory 205 may be a non-transitory memory or a data storage device, such as a hard disk drive, a solid-state disk drive, a hybrid disk drive, or other appropriate data storage, and may further store machine-readable instructions, which may be loaded and executed by the processor 207.

The processor 207 may be a single processor or multiple processors. The processor 207 may receive data from one or more components and control the operations of the one or more components based on the received or determined data. For example, the processor 207 may run the application. In some implementations, the processor 207 may be multiple processors, such as a dual processor.

The processor 207 may continuously obtain a user data stream 212 associated with an user (e.g., a data stream received from device 101 that includes information detected from one or more onboard sensors that measure vital signs and other biometric information of the user). The individual may be a human. In other embodiments, the individual may be a non-human animal. In some embodiments, data stream 212 may be a continuous data flow transmitted substantially in real-time. In other embodiments, data stream 212 may be intermittent transmission of data packets.

After receiving data stream 212, the processor 207 may determine whether a present or predicted state of the user is classified as being in the safe zone, the intermediate zone, and/or the danger zone. If it is determined that the user is at or nearing the danger zone, the current determination and/or predicted determination may be stored in memory 205 and/or may be transmitted directly to one or more third party responders (e.g., law enforcement, fire protection, or other personnel) via path 214. In some embodiments, data stream 212 may be transmitted directly to one or more third party responders (e.g., law enforcement, fire protection, or other personnel) via path 214.

The processor 207 may similarly obtain environmental information, such as one or more of carbon dioxide levels, smoke levels, presence of volatile organize compounds (VOC), or presence of airborne infectious agents. The processor 207 may also obtain other information pertaining to the user such as geographical location, geographical location of known environmentally dangerous areas, and/or regional emergency alerts.

FIG. 4 is an example process 300 implemented by a mobile device (e.g., device 103, 203) with system 100. In step 305, the processor can continuously obtain the user data stream associated with a user. The user data stream may be configured similarly as data stream 212 discussed in regard to FIG. 3. In some embodiments, the mobile device may have one or more sensors configured to detect and generate the user data stream.

In some embodiments, the user data stream may be transmitted to the mobile device by a second device. The second device may be configured similarly as device 101 discussed in regard to FIG. 2A. The second device may have one or more sensors configured to detect physiological data and generate the user data stream.

In step 310, the processor may transmit the user data stream to at least one of a cloud, a server, and/or another connected device. The processor may transmit the physiological data of the user data as part of a continuous data stream. For example, the processor may relay the user data that includes user vital signs continuously to a cloud, a server (including one or more servers related to third party responders), as well as directly to one or more third party responders (e.g., law enforcement, fire protection, other personnel, etc.), and/or another device. In response being notified that the user is not in a safe zone and/or in a danger zone, a doctor or a paramedic, for example, may be able to view the individual's vital signs, based on the user data stream, in real time.

In other embodiments, the processor may transmit user data in the form of data packets. For example, the processor may transmit the vital signs data stream taken over a 24 hour period to a cloud, a server (including one or more servers related to third party responders), as well as directly to one or more third party responders (e.g., law enforcement, fire protection, other personnel, etc.), and/or another device. In some embodiments, the user's physician may be able to remotely access the mobile wearable (e.g., the device 101) or via a cloud or a server.

In step 315, the processor may determine a safe zone of the user based on user historical records (e.g., a user's medical record and other user related information) and the user data stream. In step 320, the processor may determine whether a current and/or a predict state of the user is within the safe zone or a danger zone outside the safe zone. In some aspects, determined zones are specific to each user and can be based on measurements of the individual's heart rate, heart variable rate, oxygen saturation rate, pulse oximetry, electrocardiogram (ECG), breathing rate, blood pressure, heart arrhythmia, blood glucose, physiological boundary limits, physically falling, electroencephalography (EEG), electromyography (EMG), skin temperature, body impedance, skin conductance, loss of blood, loss of plasma, loss of blood sodium, changes in the diameter of the individuals extremities, changes in gait speed of the individual, and/or the like.

In some aspects, the processor may retrieve, from a memory (e.g., memory 105, 205), user related information to determine whether the user is or predicted to be within the safe zone and/or in the danger zone. In some aspects, factors of the safe zone include vital signs that represent the highest and lowest acceptable values from user data stream that will not trigger an alert. For example, if one of one or more vital signs for a user is a temperature of 100 degrees Fahrenheit, then a value of 100.1 degrees Fahrenheit would trigger an alert that the use is no longer in the safe zone and/or is in the danger zone, whereas 99.9 degrees Fahrenheit would not.

Other vital signs contemplated for determining and considering a user's respective safe zone, danger zone, and any other zone in classifying and predicting user states may be customized for the specific user's heart rhythm, heart variable rate, heart rate, heart variable rate, oxygen saturation rate, pulse oximetry, electrocardiogram (ECG), AFIB, VFIB, breathing rate, blood pressure, heart arrhythmia, blood glucose, anemia factors, rates of levels rapidly decreasing or increasing, physiological boundary limits, physically falling, electroencephalography (EEG), electromyography (EMG), skin temperature, body impedance, skin conductance, loss of blood, loss of plasma, loss of blood sodium, changes in the diameter of the individuals extremities, circulation factors such as leg diameter and swelling, and/or gait speed of the user.

In some aspects, environmental factors in a vicinity of the user are considered when evaluating a user's respective safe zone, danger zone, and any other zone in classifying and predicting user states, including but not limited to levels of $CO_2$, smoke, PM2.5 and PM10 (e.g., 2.5 microns and 10 microns most dangerous pollutants), volatile organic compounds/allergenic (VOC), biosensor(s) on skin surface of mosquito-borne viruses for early very critical medical intervention), a user location with respect to a user geofence boundary, alarm emergency video activated by emergency alert signals, and/or alarm emergency sound siren(s).

In some aspects, factors related to defining and evaluating one or more zones of a user may not be editable by the user. This may prevent the user from inadvertently setting the limits too low and/or too high such that the user's vital signs data during a medical emergency would not trigger an alert. Vital signs associated with defining a user's danger zone and/or safe zone may be set by a physician manually inputting vital sign boundaries into the mobile wearable (e.g., the device 101) and/or the application. In some embodiments, vital sign boundaries may be remotely set by the physician.

In some aspects, the processor may transmit, to one or more third party responders (e.g., law enforcement, fire protection, other personnel, etc.), an alert when the user is in, nearing, or predicted to be in the danger zone as defined by one or more values of the user data stream being outside vital sign boundaries. In some embodiments, the processor may additionally transmit a geographical location of the user to the one or more third party responders.

In some aspects, the processor may send, with the alert, information about the user. The information may include user identifying information such as driver's license number, social security number, mobile number, pager number, home address, work address, prescribed medication(s), blood type, allergies, primary physician's phone number, primary physician's name, hospital name and address, relatives names, relatives phone numbers, relatives addresses, medical history, and/or the like.

In some aspects, the processor may receive from a regional rapid response center a response to the transmitted alert. The response may require the user to actuate a button located on the mobile device (e.g., mobile device 103, 203) and/or the device 101 to dismiss the alert. If the individual does not actuate the button after a predetermined period of time (e.g., approximately 45 seconds, 1 min, 2 min, 5 min, etc.) the regional rapid response center may activate emergency services in response. This process is advantageous as it helps prevent false alerts due to potential sensory and/or analytical errors in devices 101, 103.

In some aspects, the geographic location or area of a user can dictate the boundaries of the safe zone, the danger zone, etc. In this respect, the processor may utilize geofencing and determine when the user is located within a predetermined geographical area. The processor may generate an alert when the user is located outside the predetermined geographical area. In some aspects, the danger zone is detected if the user has travelled outside a confined area during a hike or a walk. Upon detecting presence of the danger zone, the system can notify the user, third party responders (e.g., the police, the fire department, etc.), and/or a trusted family member (e.g., a parent). In some aspects, if the user is a child and the child has been detected as being in the danger zone by having travelled outside the safe zone (e.g., outside the house or the backyard), the system can automatically call the third party responders (e.g., the police, the fire department, medical personnel, etc.). In some aspects, users of the system can be young active children, adults, senior citizens, disabled individuals, law enforcement personnel, fire protection personnel, emergency medical personnel, hikers, skiers, hunters, field workers, long distance truck drivers, coastal area boat personnel, among others. The location of the user may be determined using a radio frequency (RF) beacon coupled to the user. In some embodiments, the location of the user may be determined using one or more sensors of devices 101, 103, including but not limited to a GPS (Global Position System) transmitter and/or use GSM (Global System for Mobile Communications). In some embodiments, devices 101 and/or 103 may incorporate G4 or G5 technology.

In some aspects, the processor may cause an audio and/or visual alert to remind the user to follow one or more aspects of a treatment protocol (e.g., take their medication). The processor may cause the mobile device (e.g., mobile device 103, 203) to issue the alert and/or the mobile wearable vital signs monitor (e.g., mobile wearable vital signs monitor 101) to issue the alert. In some embodiments, the alert may be based on recurring dosage intervals. For example, the alert may notify the user periodically according to a predetermined alert protocol (e.g., every 12 hours) to take their heart medication. In other embodiments, the alert may be in response to one or more values of the user data stream being proximal or outside the vital sign boundaries.

Figure 5:
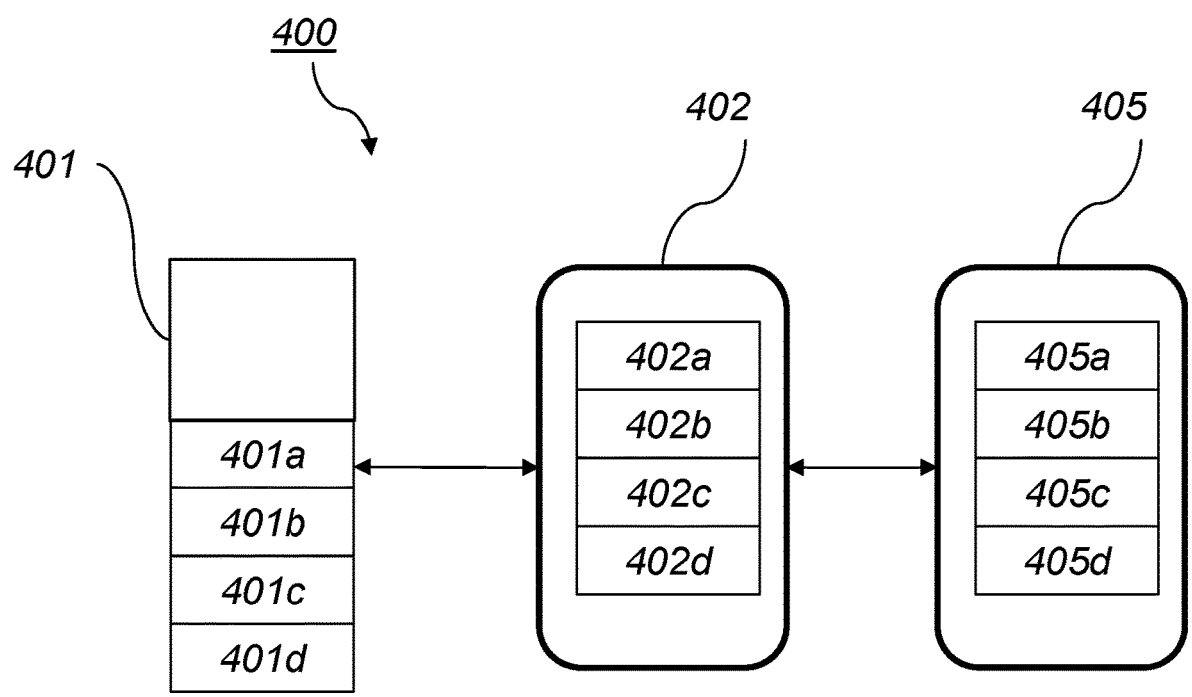
FIG. 5 illustrates another example block diagram of an example monitoring and alert system, according to an example embodiment.

FIG. 5 illustrates an block diagram of an example monitoring and alert system 400, according to an example embodiment. The system 400 can include device 401, similar to previously discussed device 101. In this respect, device 401 can be wrist wearable and configured for rapid response. Device 401 can include a transponder 401a, a rechargeable battery 401b (e.g., Lithium Ion) with a power supply to power one or more RF antennas 401c, include one or more vital sign sensor chip sets 401d, and all assembled within a biocompatible flexible band.

Device 401 can be bidirectionally coupled with a system device 402, that includes a housing with an RF antenna 402c positioned on an outer surface thereof. In some aspects, the RF antenna of device 402 can be positioned along a perimeter of an outer cover of the housing. Device 402 can include a rechargeable battery 402a, similar to device 401, and also include one or more transponders 402b such as a GPS set transponder, a user vital sign transponder, and the like. Device 402 can also include an alarm pushbutton 402d (e.g., positioned on or otherwise with an outer surface of the housing) designed to receive capacitive and/or manual input from a user. Device 402 can include a 2-way loud channel as well as a microphone and/or a speaker.

Device 402 can be connectable with one or more external computing devices (e.g., a phone as in device 103). For the hearing impaired, device 402 can also include one or more LEDs configured to actuate depending on detected user states and related zones (e.g., the housing of device 402 and/or one or more LEDs associated therewith can light up to red when the user is in the danger zone and/or outside the safe zone). Device 402 can include call notification, messages notification, alert notification, and/or the like.

Device 402 in turn can be bidirectionally coupled with a medallion 405 that can be donned by a user. Medallion 405 can include similar sensory aspects as in device 401 but simply be worn in a different location by the user (e.g., hung around the neck of the user). Medallion 405 can include a housing with an RF antenna 405c positioned on an outer surface thereof. Medallion 405 can include a rechargeable battery 405a, similar to device 401 and 402, and also include one or more transponders 405b such as a GPS set transponder, a user vital sign transponder, and the like. Medallion 405 can also include an emergency alarm pushbutton 405d with transmitter (e.g., positioned on or otherwise with an outer surface of the housing) designed to receive capacitive and/or manual input from a user. Medallion 405 can include one or more vital sign sensor chip sets, and all assembled within a biocompatible flexible band and a 2-way loud channel as well as a microphone and/or a speaker.

Figure 6:
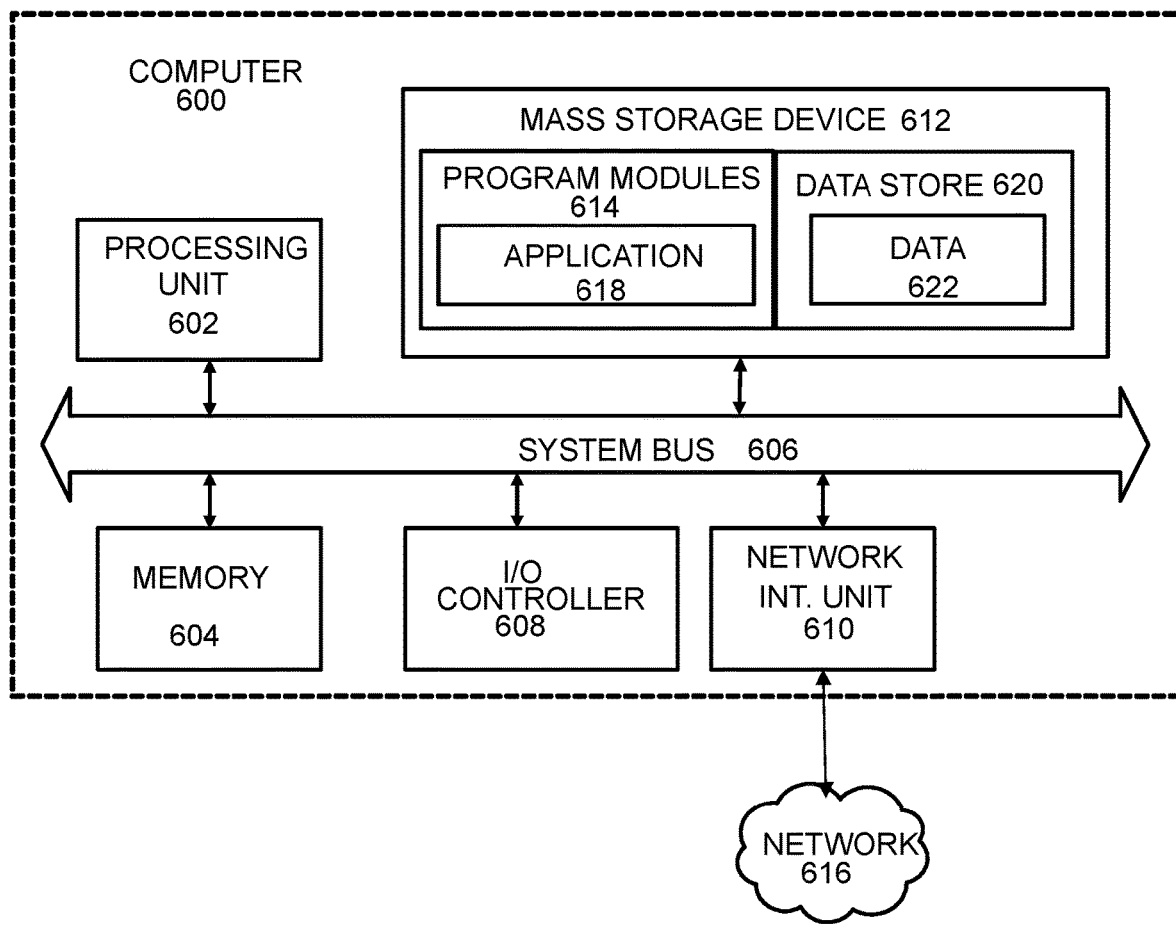
FIG. 6 is a computer architecture diagram showing a general computing system for implementing aspects of the present disclosure in accordance with one or more embodiments described herein.

FIG. 6 is a computer architecture diagram showing a general computing system capable of implementing aspects of the present disclosure in accordance with one or more embodiments described herein, such as the system 100, devices 101, 102, and 103. In any of these example implementations, computer 600 of the aforementioned may be configured to perform one or more functions associated with embodiments of this disclosure. For example, the computer 600 may be configured to perform operations in accordance with those examples shown in FIGS. 1 to 5. It should be appreciated that the computer 600 may be implemented within a single computing device or a computing system formed with multiple connected computing devices. The computer 600 may be configured to perform various distributed computing tasks, in which processing and/or storage resources may be distributed among the multiple devices. The data acquisition and display computer 650 and/or operator console 610 of the system shown in FIG. 6 may include one or more systems and components of the computer 600.

As shown, the computer 600 includes a processing unit 602 ("CPU"), a system memory 604, and a system bus 606 that couples the memory 604 to the CPU 602. The computer 600 further includes a mass storage device 612 for storing program modules 614. The program modules 614 may be operable to analyze data from any herein disclosed data feeds, classify user states based on the data feeds (e.g., user data streams that include vital sign data, location data, etc.), determine responsive actions (e.g., determine a present or predicted user state and whether to coordinate an alarm response), and/or control any related operations (e.g., transmitting one or more alert messages to first responders, coordinating a ride with emergency ride share services). The program modules 614 may include an application 618 for performing data acquisition and/or processing functions as described herein, for example to acquire and/or process any of the herein discussed data feeds. The computer 600 can include a data store 620 for storing data that may include data 622 of data feeds (e.g., data from sensors monitoring vital signs of the user, GPS data, etc.).

The mass storage device 612 is connected to the CPU 602 through a mass storage controller (not shown) connected to the bus 606. The mass storage device 612 and its associated computer-storage media provide non-volatile storage for the computer 600. Although the description of computer-storage media contained herein refers to a mass storage device, such as a hard disk or CD-ROM drive, it should be appreciated by those skilled in the art that computer-storage media can be any available computer storage media that can be accessed by the computer 600.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 600. "Computer storage media", "computer-readable storage medium" or "computer-readable storage media" as described herein do not include transitory signals.

According to various embodiments, the computer 600 may operate in a networked environment using connections to other local or remote computers through a network 616 (e.g., previous network 108) via a network interface unit 610 connected to the bus 606. The network interface unit 610 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 600 may also include an input/output controller 608 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 600. The bus 606 may enable the processing unit 602 to read code and/or data to/from the mass storage device 612 or other computer-storage media.

The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state or may include rotating media storing magnetically-encoded information. The program modules 614, which include the data feed application 618, may include instructions that, when loaded into the processing unit 602 and executed, cause the computer 600 to provide functions associated with one or more embodiments illustrated in the figures of this disclosure. The program modules 614 may also provide various tools or techniques by which the computer 600 may participate within the overall systems or operating environments using the components, flows, and data structures discussed throughout this description.

In general, the program modules 614 may, when loaded into the processing unit 602 and executed, transform the processing unit 602 and the overall computer 600 from a general-purpose computing system into a special-purpose computing system. The processing unit 602 may be constructed from any number of transistors or other discrete circuit elements, which may individually or collectively assume any number of states. More specifically, the processing unit 602 may operate as a finite-state machine, in response to executable instructions contained within the program modules 614. These computer-executable instructions may transform the processing unit 602 by specifying how the processing unit 602 transitions between states, thereby transforming the transistors or other discrete hardware elements constituting the processing unit 602.

Encoding the program modules 614 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer storage media are implemented as semiconductor-based memory, the program modules 614 may transform the physical state of the semiconductor memory, when the software is encoded therein. For example, the program modules 614 may transform the state of transistors, capacitors, or other discrete circuit elements constituting the semiconductor memory.

As another example, the computer storage media may be implemented using magnetic or optical technology. In such implementations, the program modules 614 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

According to certain embodiments, the above-described data feeds may be stored in databases such as database servers that store master data, event related data, response plan data, telemetry information, and mission data as well as logging and trace information. The databases may also provide an API and/or API access (e.g., for open source) to the web server for data interchange based on JSON specifications. In some embodiments, the database may also directly interact with systems and monitoring devices to identify, determine, and control response operations. According to certain embodiments, the database servers may be optimally designed for storing large amounts of data, responding quickly to incoming requests, having a high availability and historizing master data.

In the description herein, numerous specific details are set forth. However, it is to be understood that embodiments of the present disclosure may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the present disclosure so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form. Accordingly, "a drone" or "the drone" may refer to one or more drones where applicable.

Unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Certain embodiments of the present disclosure are described above with reference to block and flow diagrams of systems and methods and/or computer program products according to example embodiments of the present disclosure. It will be understood that one or more blocks of the block diagrams and flow diagrams, and combinations of blocks in the block diagrams and flow diagrams, respectively, may be implemented by computer-executable program instructions. Likewise, some blocks of the block diagrams and flow diagrams may not necessarily need to be performed in the order presented, or may not necessarily need to be performed at all, according to some embodiments of the present disclosure.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that may direct a computer or other programmable data processing apparatus to function in a particular manner, such that the instructions stored in the computer-readable memory produce an article of manufacture including instruction means that implement one or more functions specified in the flow diagram block or blocks.

As an example, embodiments of the present disclosure may provide for a computer program product, including a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Various aspects described herein may be implemented using standard programming and/or engineering techniques to produce software, firmware, hardware, and/or any combination thereof to control a computing device to implement the disclosed subject matter. A computer-readable medium may include, for example: a magnetic storage device such as a hard disk, a floppy disk or a magnetic strip; an optical storage device such as a compact disk (CD) or digital versatile disk (DVD); a smart card; and a flash memory device such as a card, stick or key drive, or embedded component. Additionally, it should be appreciated that a carrier wave may be employed to carry computer-readable electronic data including those used in transmitting and receiving electronic data such as streaming video or in accessing a computer network such as the Internet or a local area network (LAN). Of course, a person of ordinary skill in the art will recognize many modifications may be made to this configuration without departing from the scope or spirit of the claimed subject matter.

In some aspects, the systems and methods of this disclosure will advantageously reduce the cost of health care as well as the cost of third party responders, such as police and fire protection services. In some aspects, with the wearable monitor, the herein disclosed continuous physiological data stream of a user can be provided so that intervention, by a user and/or third party responders, can take action while in the early stages of illness or disease (e.g., based on detection of presence of safe zone, intermediate zone, and danger zone) to prevent more acute and costly issues later on. This not only enhances the quality of a user's life with disease management but also advantageously reduces the cost and resources of healthcare. In some aspects, PUMAS will enable a change in the health care system shifting towards wearable health-care systems focused on the user. Additionally, the systems and methods of this disclosure allow both users and health care personnel to focus on preventative health care thus further reducing the cost of health care.

Further advantages of the systems and methods of this disclosure include a reduction in the cost of care to the chronically ill, improved global and local public health surveillance, monitoring and reduction in epidemics, increased control over infectious disease and improved drug safety. The systems and methods of this disclosure also permits a diminished rate of medical errors, better customer service in healthcare, ongoing preventative health with attendant reductions in morbidity, disability, mortality, a reduction in the cost of care and safer and more effective clinical trials.

The systems and methods of this disclosure also provides targeted and more effective advertising to categories of users such as senior citizens, people with specific chronic health problems, field, fire and police workers, hikers, skiers, hunters, among others. For example, if a user enjoys hiking, as evident from the user frequenting trails, the systems and methods of this disclosure may provide advertising of hiking equipment to that user.

While certain embodiments of the present disclosure have been described in connection with what is presently considered to be the most practical and various embodiments, it is to be understood that the present disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the present disclosure, including the best mode, and also to enable any person skilled in the art to practice certain embodiments of the present disclosure, including making and using any devices or systems and performing any incorporated methods. The patentable scope of certain embodiments of the present disclosure is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for monitoring a user and coordinating one or more alert response by one or more first responders and configured to connect to one or more monitoring devices and comprising:
    a mobile device configured to perform operations comprising:
    obtain user data from a continuous dynamic user data stream from the one or more monitoring devices;
    determine, based on the continuous dynamic user data stream and static user historical records, a user-specific safe zone of the user; and
    determine, based on the continuous dynamic user data stream and the static user historical records, whether a current state or a predicted state of the user is within the user-specific safe zone and/or a user-specific danger zone defined as being outside the user-specific safe zone.

2. The system of claim 1, wherein the operations comprise:
    analyze the continuous dynamic user data stream based on defined parameters of the user-specific safe zone related to the user; and
    alert the user and/or the one or more first responders when the data or information is outside the user-specific safe zone.

3. The system of claim 2, wherein the operations further comprise:
    if the user is not within the user-specific safe zone and/or is within the user-specific danger zone, then transmit to the one or more first responders one or more monitoring device generated diagnostics, user medical records, imaging records, previous doctor's assessment and/or intervention(s), user health informatics data records, and/or a geographical location of the user.

4. The system of claim 2, wherein the operations further comprise:
    if the user is not within the user-specific safe zone and/or is within the user-specific danger zone, then automatically establish, by the one or more monitoring devices, 2-way communication between the user and the one or more first responders.

5. The system of claim 2, wherein the operations further comprise:
    if the user fails to respond to the alert within a predetermined period of time, then transmit, by the one or more monitoring devices and/or a user computing device, an emergency alert signal to the one or more first responders.

6. The system of claim 2, wherein the operations further comprise: receive, from the one or more first responders, a response to the alert, the one or more first responders comprising at least a rapid response center configured to coordinate one or more response with a law enforcement department, a fire department, a hospital, a private medical center, a doctor, a neighbor, and/or an emergency contact of the user.

7. The system of claim 2, wherein the operations comprise:
    apply a machine learning model to generate one or more predictions of the safe zone and/or the danger zone of the user based on a zone criteria presence of the user data, the one or more predictions comprising a binary output to indicate a plurality of relevant diagnostic features based on medical metadata of the user data, the machine learning model having been developed using the continuous user data stream, archived user data, and prospective user data.

8. The system of claim 1, wherein vital signs considered in determining user specific safe and danger zones, determining and/or predicting user states, and/or zone classification comprise heart rate, heart variable rate, oxygen saturation rate, pulse oximetry, electrocardiogram (ECG), breathing rate, blood pressure, heart arrhythmia, blood glucose, physiological boundary limits, physically falling, electroencephalography (EEG), electromyography (EMG), skin temperature, blood alcohol, other substance levels in blood, body impedance, skin conductance, loss of blood, loss of plasma, loss of blood sodium, changes in the diameter of the individuals extremities, and/or gait speed.

9. The system of claim 1, wherein the one or more monitoring devices comprise a heart monitor, a watch, a pulse monitor, a glucose sensor, a smartphone, a wrist bracelet, a ring, a medallion, a pendant, and/or a smartphone case, and wherein the one or more monitoring devices at least comprise a rechargeable battery, memory, and a transponder to bidirectionally communicate with one or more external computing devices.

10. The system of claim 1, wherein one or more boundaries of the user-specific safe zone, a user-specific intermediate zone, and/or the user-specific danger zone of the user are not editable by the user.

11. The system of claim 10, wherein the operations comprise generate the continuous dynamic user data stream based on data from one or more sensors of the one or more monitoring devices, the one or more sensors being configured to detect vital signs and/or location associated with the user, the one or more monitoring devices comprising a wearable device wearable by the user and/or a mobile computing device.

12. The system of claim 1, wherein the user-specific safe zone is determined by determining, based on location data of the continuous dynamic user data stream, when the user is located within a predetermined geographical area; and generating an alert that the user is no longer in the user-specific safe zone and/or is in the user-specific danger zone when the user is detected as being located outside the predetermined geographical area.

13. The system of claim 12, wherein the one or more monitoring devices comprise a wearable device donned by the user, and wherein a location of the user is determined using a radio frequency (RF) beacon coupled to the wearable device donned by the user wherein the wearable device is a wrist bracelet, a tag, a ring, a medallion, a garment, and/or a pendant.

14. A method for monitoring a user and coordinating one or more alert response by one or more first responders, comprising:
  obtaining, by a processor, user data from a continuous dynamic user data stream from the one or more monitoring devices;
  determine, by the processor and based on the continuous dynamic user data stream and static user historical records, a safe zone of the user; and
  determine, by the processor and based on the continuous dynamic user data stream and the static user historical records, whether a current state or a predicted state of the user is within the user-specific safe zone and/or a user-specific danger zone defined as being outside the user-specific safe zone.

15. The method of claim 14, further comprising:
  analyzing, by the processor, the continuous dynamic user data stream based on defined parameters of the user-specific safe zone related to the user; and
  alerting, by the processor, the user and/or a third party when the data or information is outside the user-specific safe zone.

16. The method of claim 14, wherein the user-specific safe zone is determined by determining, based on location data of the continuous dynamic user data stream, when the user is located within a predetermined geographical area; and generating an alert that the user is no longer in the user-specific safe zone and/or is in the user-specific danger zone when the user is detected as being located outside the predetermined geographical area.

17. The method of claim 14, further comprising receiving, from the one or more first responders, a response to the alert, the one or more first responders comprising at least a rapid response center configured to coordinate one or more response with a law enforcement department, a fire department, a hospital, a private medical center, a doctor, a neighbor, and/or an emergency contact of the user.

18. The method of claim 14, further comprising: generating the continuous dynamic user data stream based on data from one or more sensors of the one or more monitoring devices, the one or more sensors detecting vital signs and/or location associated with the user, the one or more monitoring devices comprising a wearable device wearable by the user and/or a mobile computing device; and
  if the user is not within the user-specific safe zone and/or is within the user-specific danger zone, then transmitting to the one or more first responders one or more monitoring device generated diagnostics, user medical records, imaging records, previous doctor's assessment and/or intervention(s), user health informatics data records, and/or a geographical location of the user.

19. The method of claim 14, further comprising:
if the user is not within the user-specific safe zone and/or is within the user-specific danger zone, then automatically establishing, by the one or more monitoring devices, 2-way communication between the user and the one or more first responders.

20. The method of claim 14, further comprising:
if the user fails to respond to the alert within a predetermined period of time, then transmitting, by the one or more monitoring devices and/or a user computing device, an emergency alert signal to the one or more first responders.

* * * * *